United States Patent
Miller

(10) Patent No.: US 12,115,222 B2
(45) Date of Patent: Oct. 15, 2024

(54) COMPOSITIONS AND METHODS FOR IMPROVING THE SOLUBILITY OF ERECTILE DYSFUNCTION THERAPEUTICS

(71) Applicant: Villya LLC, Melbourne, FL (US)

(72) Inventor: William Lee Miller, Melbourne, FL (US)

(73) Assignee: Villya LLC, Melbourne, FL (US)

( * ) Notice: Subject to any disclaimer, the term of this patent is extended or adjusted under 35 U.S.C. 154(b) by 0 days.

(21) Appl. No.: 18/592,795

(22) Filed: Mar. 1, 2024

(65) Prior Publication Data

US 2024/0269297 A1   Aug. 15, 2024

Related U.S. Application Data

(63) Continuation of application No. PCT/US2024/012409, filed on Jan. 22, 2024.

(60) Provisional application No. 63/517,600, filed on Aug. 3, 2023, provisional application No. 63/459,761, filed on Apr. 17, 2023, provisional application No. 63/443,546, filed on Feb. 6, 2023, provisional application No. 63/481,050, filed on Jan. 23, 2023.

(51) Int. Cl.
*A61K 47/54* (2017.01)
*A61K 9/08* (2006.01)
*A61K 47/10* (2017.01)

(52) U.S. Cl.
CPC .............. *A61K 47/549* (2017.08); *A61K 9/08* (2013.01); *A61K 47/10* (2013.01)

(58) Field of Classification Search
CPC .................................................. A61K 47/549
See application file for complete search history.

(56) References Cited

U.S. PATENT DOCUMENTS

| | | | |
|---|---|---|---|
| 6,159,932 A | 12/2000 | Mencke et al. | |
| 6,224,573 B1 | 5/2001 | Yeager et al. | |
| 6,416,779 B1 | 7/2002 | D'Augustine et al. | |
| 7,258,873 B2 | 8/2007 | Truong-Le et al. | |
| 8,034,765 B2 | 10/2011 | De et al. | |
| 8,461,115 B2 | 6/2013 | Uttenthal | |
| 8,551,507 B2 | 10/2013 | Liu | |
| 8,840,869 B2 | 9/2014 | Friedman et al. | |
| 9,333,329 B2 | 5/2016 | Ziv | |
| 10,201,576 B2 | 2/2019 | Rishi | |
| 10,350,042 B2 | 7/2019 | Schuman et al. | |
| 10,391,134 B2 | 8/2019 | Meuwly et al. | |
| 10,555,900 B2 | 2/2020 | Podolski et al. | |
| 10,662,259 B2 | 5/2020 | Russo et al. | |
| 10,857,151 B1 | 12/2020 | Miller | |
| 11,364,203 B2 | 6/2022 | Vodak et al. | |
| 2002/0081292 A1 | 6/2002 | Jancys | |
| 2002/0147201 A1 | 10/2002 | Chen et al. | |
| 2004/0198676 A1 | 10/2004 | Soll et al. | |
| 2006/0111571 A1 | 5/2006 | Wizel et al. | |
| 2006/0147388 A1 | 7/2006 | Merkus et al. | |
| 2006/0292225 A1 | 12/2006 | Felix et al. | |
| 2009/0018175 A1 | 1/2009 | Kanari et al. | |
| 2009/0036458 A1 | 2/2009 | Fattohi et al. | |
| 2011/0033525 A1 | 2/2011 | Liu | |
| 2012/0329738 A1 | 12/2012 | Liu | |
| 2014/0094418 A1 | 4/2014 | Isele | |
| 2015/0359898 A1 | 12/2015 | Purandare et al. | |
| 2016/0083385 A1 | 3/2016 | Liu et al. | |
| 2016/0272636 A1 | 9/2016 | Qian et al. | |
| 2019/0160332 A1 | 5/2019 | Beer et al. | |
| 2019/0223481 A1 | 7/2019 | Gaspard et al. | |
| 2019/0290474 A1 | 9/2019 | Simpson et al. | |
| 2021/0068425 A1 | 3/2021 | Ross et al. | |
| 2021/0260062 A1 | 8/2021 | Miller | |
| 2022/0047506 A1 | 2/2022 | Miller | |
| 2022/0142920 A1 | 5/2022 | Miller | |

FOREIGN PATENT DOCUMENTS

| | | |
|---|---|---|
| CN | 105816421 B | 1/2019 |
| CN | 110128429 A | 8/2019 |
| DE | 3619030 A1 | 12/1987 |
| EP | 3868381 A1 | 8/2021 |
| KR | 20160017798 A | 2/2016 |
| RU | 2681214 C1 | 3/2019 |
| WO | WO-99/41233 A1 | 8/1999 |
| WO | WO-2000/078149 A1 | 12/2000 |
| WO | WO-01/49268 A1 | 7/2001 |

(Continued)

OTHER PUBLICATIONS

Abou-Taleb et al., "Vardenafil Oral Dispersible Films (ODFs) with Advanced Dissolution, Palatability, and Bioavailability," *pharmaceutics*, vol. 14, No. 517, 17 pages, 2022.

May 24, 2024—(WO) International Search Report and Written Opinion—App PCT/US2024/012409.

May 24, 2024—(WO) International Search Report and Written Opinion—App PCT/US2024/012426.

Kharisma et al., "Dissolution Rate Repairing of Simvastatin as A New Approach in Cocrystallization," *Der Pharmacia Lettre*, vol. 9, No. 6, pp. 17-28, 2017.

Ganesan et al., "Solubility: a speed-breaker on the drug discovery highway," *Bioequiv. Availab.* vol. 3, No. 3, pp. 56-58, 2017.

(Continued)

*Primary Examiner* — Rei Tsang Shiao

(74) *Attorney, Agent, or Firm* — BANNER & WITCOFF, LTD.

(57) ABSTRACT

A method is disclosed for improving the solubility of a poorly soluble drug compound such as by mixing the poorly water-soluble drug compound (such as alprostadil, sildenafil, tadalafil, vardenafil, avanafil, or a pharmaceutically acceptable salt of any thereof) with a non-nutritive sugar such as rubusoside, rebaudioside A, dulcoside B, dodecyl-β-D-maltoside (DDM), or stevioside, or any combination thereof in the presence of a pharmaceutically acceptable solvent such as ethanol and then removing the solvent to creating a water-soluble drug-sugar complex.

29 Claims, 1 Drawing Sheet

(56) References Cited

FOREIGN PATENT DOCUMENTS

| WO | WO-2007/011349 A1 | 1/2007 |
|---|---|---|
| WO | WO-2008/077130 A2 | 6/2008 |
| WO | WO-2009/109966 A1 | 9/2009 |
| WO | WO2011030351 * | 3/2011 |
| WO | WO-2011/047227 A2 | 4/2011 |
| WO | WO-2011/098579 A1 | 8/2011 |
| WO | WO-2014-152382 A1 | 9/2014 |
| WO | WO-2015/071668 A1 | 5/2015 |
| WO | WO-2016/090240 A1 | 6/2016 |
| WO | WO-2016/143939 A1 | 9/2016 |
| WO | WO-2020/061584 A1 | 3/2020 |

OTHER PUBLICATIONS

*Absorption and distribution of steviol glycosides in animal and human models.* Stevia Technology. Retrieved Jul. 31, 2023, from www.steviashantanu.com/single-post/2015/11/18/absorption-and-distribution-of-steviolglycosides-in-animal-and-human-models.
Savjani et al. "Drug Solubility: Importance and Enhancement Techniques," *ISRN Pharm.*, 2012, doi: 10.5402/2012/195727.
Jun. 2011, Pharmaceutical Issues when Crushing, Opening or Splitting Oral Dosage Forms, by the Royal Pharmaceutical Society. www.rpharms.com/Portals/0/RPS%20document%20library/Open%20access/Support/toolkit/phar maceuticalissuesdosageforms-%282%29.pdf <http://www.rpharms.com/Portals/0/RPS%20document%20library/Open%20access/Support/toolkit/pharmaceuticalissuesdosageforms-%282%29.pdf.
Schiffman et al., "Sucralose, A Synthetic Organochlorine Sweetener: Overview of Biological Issues," *J. Toxicol. Environ. Health B. Crit. Rev.* 16(7): 399-451, 2013.
Yuma et al., "Allulose for the attenuation of postprandial blood glucose levels in healthy humans: A systematic review and meta-analysis," *PLoS One* 18(4): e0281150, 2023.
Moreton, C., "Poor Solubility—Where do we stand 25 years after the 'Rule of Five'?" *Amer. Pharm. Rev.* (2021).
Patel et al., "Formulation and Development Strategies for Drugs Insoluble in Gastric Fluid," *International Research Journal of Pharmacy*, 2012, 3 (1), pp. 106-113.
Jatwani et al., "An Overview on Solubility Enhancement Techniques for Poorly Soluble Drugs and Solid Dispersion as An Eminent Strategic Approach," *International Journal of Pharmaceutical Sciences and Research*, 2012, vol. 3(4), pp. 942-956.
Nov. 17, 2021—(WO) Notification of Transmittal of the International Search Report and Written Opinion—Appl No. PCT/US2021/044665.
Liu et al., "Dissolution and oral bioavailability enhancement of praziquantel by solid dispersions," *Drug Delivery and Translational Research*, vol. 8 (Feb. 15, 2018), pp. 580-590.
Pakharukova et al., "The first comprehensive study of praziquantel effects in vivo and in vitro on European liver fluke *Opisthorchis felineus* (Trematoda)," *International Journal of Antimicrobial Agents*, vol. 46, (Jul. 2015), pp. 94-100.
Jeon et al., "Differential diagnosis of Taenia asiatica using multiplex PCR," *Experimental Parasitology*, vol. 121 (Nov. 5, 2008), pp. 151-156.
Gaggero et al., "Cogrinding with surfactants as a new approach to enhance in vitro dissolution of praziquantel," *Journal of Pharmaceutical and Biomedical Analysis*, vol. 189, 12 pages, 2020.
Holvoet et al., "Preparation and evaluation of paclitaxel-containing liposomes," *Die Pharmazie—An International Journal of Pharmaceutical Sciences*, vol. 62, pp. 126-132, 2007.
Kannan et al., "Effect of sucrose as a lyoprotectant on the integrity of paclitaxel-loaded liposomes during lyophilization," *Journal of Liposome Research*, Early Online, pp. 1-9, 2014.
Yang et al., "Liposome Formulation of Paclitaxel with Enhanced Solubility and Stability," *Drug Delivery*, vol. 14, pp. 301-308, 2007.

Zhang et al., "A Novel Solubility-Enhanced Rubusoside-Based Micelles for Increased Cancer Therapy," *Nanoscale Research Letters*, vol. 12, No. 274, 10 pages, 2017.
English Translation of WO 2016/143939 publication of PCT/KR2015/003643.
"Female Genital Schistosomiasis, A Pocket Atlas for Clinical Health-Care Professionals," WHO Library Cataloguing-in-Publication-Data, 2015.
"Treatment of FGS with Praziquantel" https://clinicaltrials.gov/ct2/show/ NCT04115072 at https://clinicaltrials.gov/ct2/show/NCT04115072 (retrieved from the internet Jul. 8, 2020) (Year: 2019).
Alexander et al. "Why consider vaginal drug administration?" *Fertility and Sterility*; vol. 82; No. 1; Jul. 2004; pp. 1-12.
Zanolla et al. "A new soluble and bioactive polymorph of praziquantel" *European Journal of Pharmaceutics and Biopharmaceutics*, 127 (2018) 19-28.
Bribeche et al. "Topical praziquantel as a new treatment for perioral dermatitis: results of a randomized vehicle-controlled pilot study" *Clinical and Experimental Dermatology*; (2014) 39, pp. 448-453.
Goodman & Gilman's, *The Pharmacological Basis of Therapeutics* (Tenth Edition (2001), McGraw Hill, Chapter 1, pp. 3-29 (Year: 2001).
Hotez et al. "Female genital schistosomiasis and HIV/AIDS: Reversing the neglect of girls and women" *PLoS Neglected Tropical Diseases*, (2019).
Abla et al. "Evaluation of the pharmacokinetic-pharmacodynamic relationship of praziquantel in the Schistosoma mansoni mouse model" *PLoS Neglected Tropical Diseases*, Sep. 21, 2017.
El-Feky et al. "Praziquantel in a Clay Nanoformulation Shows More Bioavailability and Higher Efficacy against Murine Schistosoma mansoni Infection" *Antimicrobial Agents and Chemotherapy*, Jun. 2015, vol. 59, No. 6, pp. 3501-3508.
Kjetland et al. "Genital schistosomiasis in women: a clinical 12-month in vivo study following treatment with praziquantel" *Transactions of the Royal Society of Tropical Medicine and Hygiene*, vol. 100, No. 8, Aug. 1, 2006, pp. 740-752.
Jul. 27, 2021—(EP) Extended European Search Report and Search Opinion—Appln. No. 21158508.8.
Rowe et al., "Propylene Glycol" Handbook of Pharmaceutical Excipients; 6th ed.; Pharmaceutical Press; Published 2009; pp. 592-594.
Pearson, "Schistosomiasis (Bilharziasis)" Merck Manuals Professional Edition; Revised May 2018.
Zou et al. "Application of Pharmacokinetic-Pharmacodynamic Modeling in Drug Delivery: Development and Challenges" *Frontiers in Pharmacology*, Published Jul. 3, 2020; vol. 11; No. 997.
Block "Chapter 29: Medicated Topicals" *Remington Essentials of Pharmaceutics*; Edited by Linda Felton; Pharmaceutical Press; 1st edition; pp. 565-579; Published 2013.
Shelley Fox; "Remington Education: Pharmaceutics" Pharmaceutical Press; 1st edition; p. 1-17; 2014.
Extended European Search Report issued Jul. 27, 2021 in European Patent Application No. 21158508.8.
Communication under Rule 71(3) EPC—Intention to Grant issued Feb. 27, 2023 in European Patent Application No. 21158508.8.
Brotto, V. et al. Clinical Dosage Calculations, 3rd edition. Cengage Learning Australia, 2019: 98-117. (Year: 2019).
Hloch, S. et al. Advances in Manufacturing Engineering and Materials. Springer International Publishing, 2018: 66-67. (Year: 2018).
Srikrishna, S. et al. "The vagina as a route for drug delivery: a review." *International urogynecology journal*, 2013. vol. 24,4: 537-43. (Year: 2013).
Fulcher, E. M. et al. Pharmacology, 3rd edition, 2011. Elsevier Health Science: 39-52 (Year: 2011).
Wen, H. et al. Oral Controlled Release Formulation Design and Drug Delivery: Theory to Practice. Wiley, 2011 :121. (Year: 2011).
Non-Final Office Action issued Oct. 5, 2023 in U.S. Appl. No. 17/109,531.
Final Office Action issued Jan. 10, 2024 in U.S. Appl. No. 17/109,531.
U.S. Appl. No. 17/109,531, filed Dec. 2, 2020 (US Pub. 2021-0260062).

(56) References Cited

OTHER PUBLICATIONS

Liu, Zhijun et al: "Cytotoxic and antiangiogenic paclitaxel solubilized and permeation-enhanced by natural product nanoparticles", *Anti-Cancer Drugs*, [Online] vol. 26, No. 2, Feb. 1, 2015 (Feb. 1, 2015), pp. 167-179.

Atipairin et al., "Development of a sildenafil citrate microemulsion-loaded hydrogel as a potential system for drug delivery to the penis and its cellular metabolic mechanism," *Pharmaceutics*, 12(11): 1055 (2020).

* cited by examiner

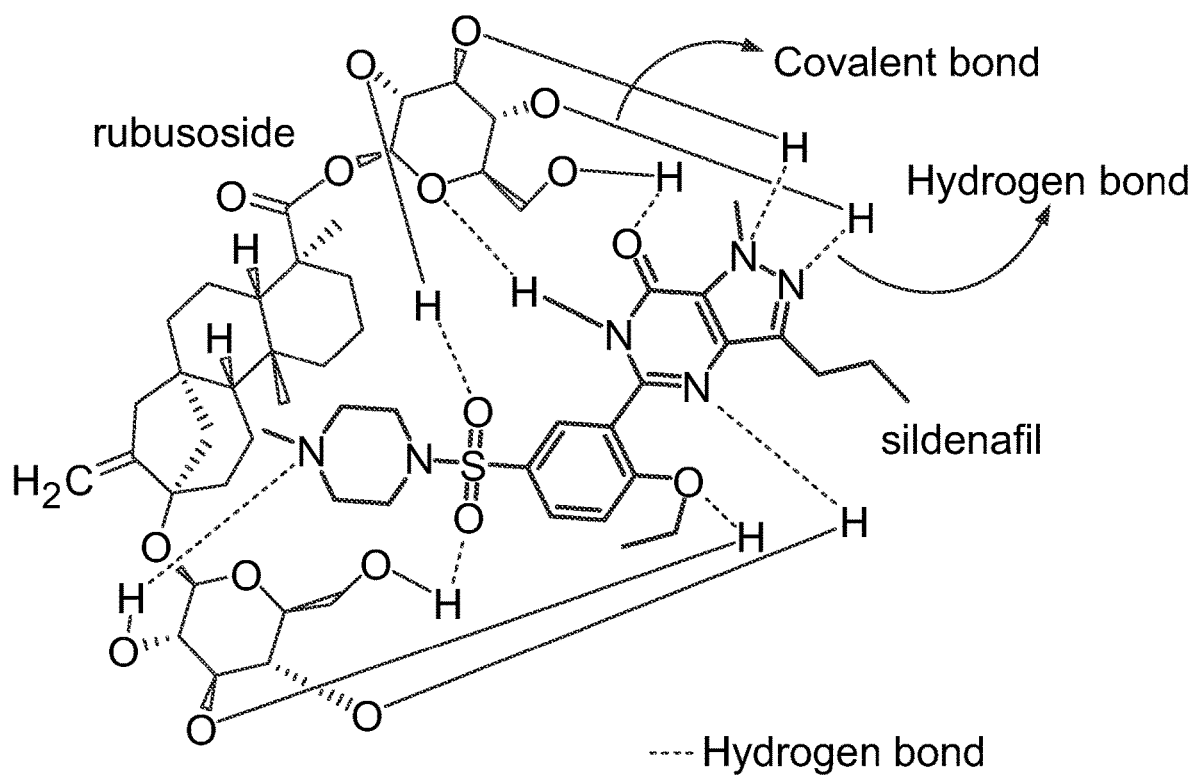

COMPOSITIONS AND METHODS FOR IMPROVING THE SOLUBILITY OF ERECTILE DYSFUNCTION THERAPEUTICS

RELATED APPLICATIONS

This application is a 35 U.S.C. § 111 continuation application of International PCT Application PCT/US24/12409 filed on Jan. 22, 2024, which claims benefit to U.S. Provisional applications 63/517,600, 63/481,050, 63/443,546, and 63/459,761 filed respectively on Aug. 3, 2023, Apr. 17, 2023, Feb. 6, 2023 and Jan. 23, 2023; the contents of each of which are incorporated herein by reference in their entirety.

TECHNICAL FIELD

Disclosed are water-soluble compound-sugar complexes comprised of a non-nutritive sugar, such as a diterpene di-glycoside ("DTG"), triterpene glycoside, or other listed sugar, with a poorly soluble drug, its salt or free form of the drug or its pharmaceutically acceptable salt, wherein the formed water-soluble complex of the sugar and the compound significantly enhances the solubility of the poorly soluble drug for administration to a subject. Also disclosed are methods for making such complexes and pharmaceutical compositions comprising such complexes.

BACKGROUND

The solubility of many compounds can play a critical role in their commercial utility, especially in the pharmaceutical industry. Water solubility of a drug plays an important role in the compound's effectiveness as a drug, especially in a number of essential pharmacokinetic (PK) properties. Drugs with poor water solubility can lead directly to insufficient uptake, poor $C_{max}$ properties (e.g., maximum blood concentration), and the like. If a drug is not sufficiently water soluble, it may not be fully absorbed into a subject's blood circulation, which leads to insufficient $C_{max}$ to be efficacious (e.g., Ganesan et al., "Solubility: a speed-breaker on the drug discovery highway," *Bioequiv. Availab.* 3(3): 56-8, 2017, Editorial).

It is well known that many commercially available erectile dysfunction (ED) drugs generally have poor water solubility. A water-soluble drug dissolves at an amount above 10 mg/mL at physiological pH and 37° C. A poorly water-soluble drug is any drug that dissolves at an amount below 1 mg/mL at physiological pH and at 37° C. Sildenafil citrate (SLC), which is sold under the brand names Viagra® and Revatio®, and is considered to have a low water-solubility water solubility resulting in a delayed onset of action and/or poor bioavailability when administered to a subject (i.e, it is water soluble at 4.1±1.3 mg/ml in distilled water). Tadalafil (Cialis®) has been considered practically insoluble in water, which has caused highly fluctuating blood levels and unreproducible clinical effects. Vardenafil HCl (under brand names Levitra® or Staxyn®) has a water solubility of 0.11 mg/mL, which has caused variability in the drug response in a given subject administered vardenafil. Avanafil (under the brand name Stendra®) has a water solubility of less than 1.0 mg/mL at 25° C. and less than 1 mg/mL in ethanol at 25° C.

In each case, the poor water solubility of erectile dysfunction ("PWS-ED") drugs has had a negative impact on the use of these drugs either because of the lack of reproducible results and/or the slow onset of activity.

Still further, alprostadil, another ED drug, has also been used for temporary patency of ductus arteriosus in newborns with congenital heart diseases before surgical intervention. It is a phosphodiesterase-5 inhibitor like sildenafil. It is administered as an injection as well as in the form of a suppository. It has also been formulated into a topical cream with skin-permeation enhancing drug delivery (Vitaros® cream).

Identifying a methodology that renders poorly soluble drugs substantially more soluble in aqueous environments can rescue drugs that showed promise in treating diseases but were commercially unviable due to insufficient solubility.

SUMMARY

Finding new means of making existing poorly water-soluble ("PWS") erectile dysfunction ("ED") drugs PWS-ED drugs more soluble has been long sought for both FDA-approved ED drugs as well as other drugs. Disclosed are water-soluble complexes of a non-nutritive sugar such as a diterpene di-glycoside or another non-nutritive sugar described herein with a PWS-ED drug, wherein the complex significantly enhances the solubility of poorly water-soluble ED drugs in vitro. The sugar-compound complex can employ a single sugar or a combination of two or more of the indicated sugars. One embodiment contemplates making a water-soluble sugar-drug complex using one or two sugars at a ratio of about 1 to about 10 moles of sugar to each mole of drug as well as any value between one and ten. Also disclosed are methods for making such complexes and pharmaceutical compositions comprising such complexes.

Provided herein are methods of improving the water solubility of a PWS-ED drug by a means that creates stable complexes of the drug with a sugar where such stability is as defined herein. Without being limited to any theory, the stability of these complexes is believed to be based on hydrophilic hydrogen bonds and/or host-guest chemistry between the drug and a sugar. In effect, the methods create a stable complex between a pharmaceutically acceptable sugar form of a drug for delivery (e.g., oral delivery) to a subject in need thereof. In the instance of host-guest chemistry, the compounds join together to form a complex, wherein one compound in the complex is the host and one is the guest. In some cases, in addition to the hydrophilic hydrogen bonds, hydrophobic interactions such as van der Waals interactions between the drug and the sugar, may be involved which can further enhance the stability of the complex comprising the host and guest together.

Typically, the art has shown that drug solubility is frequently improved via specific salt formation of the compound over its free form. While such modifications can enhance a drug's solubility, the resulting salt may still be considered poorly water-soluble. Accordingly, the methods and complexes described herein can be used with the PWS-ED drugs where poor water solubility is found in a free base or acid or its salt form.

Provided herein are complexes comprising one or more of the disclosed sugars, such as a diterpene di-glycoside (DTG) or stevioside and stevia (examples of triterpenes), and a poorly water soluble erectile dysfunction (ED) drug (i.e., poorly soluble or insoluble drug, "PWS-ED drug"), wherein the solubility of the complex is significantly enhanced as compared to the PWS-ED drug alone (e.g., not in the complex created by the disclosed methods). In some cases, a moderately soluble (having a solubility of less than 10 mg/mL or considered poorly water-soluble) compound can be made more soluble by complexation with a sugar as defined herein at the same ratios of sugar and compound as set forth herein. Such is particularly important for topical application for the solubility of a compound as it transport across the skin barrier for purposes of in vivo update. Alprostadil is considered water insoluble or poorly water-soluble having less than 1 mg/ml solubility. Exemplary erectile dysfunction drugs include the free form of alprostadil, avanafil, sildenafil, tadalafil, and vardenafil, their pharmaceutically acceptable salts, pro-drugs, and polymorphs thereof. The complexes described herein employ PWS-ED drugs which are generally pharmaceutical compounds having at least one heteroatom capable of forming a hydrogen bond with the DTG or non-nutritive sugar. Not to be bound by theory, but it is believed that the formed complex forms via non-covalent hydrogen bonding and optionally hydrophobic-hydrophobic interactions, such as van der Waal forces.

As is well known, the sugar portion of a DTG has a plurality of hydroxyl functionality capable of forming hydrogen bonds. In some cases, certain sugars may also contain a carboxyl group (e.g., sialic acid, glucuronic acid, etc.), an amino group (e.g., glucosamine), or a N-acetyl group (e.g., N-acetylglucosamine), each of which is capable of forming hydrogen bonds. The presence of such functionality allows DTGs to participate in hydrogen bonding with a drug compound containing at least one heteroatom that is capable of forming hydrogen bonds with the DTG.

One embodiment disclosed is a method of improving a compound's water solubility which method comprises: admixing (e.g., stirring) the PWS-ED drug with a sugar in a solvent or co-solvent (e.g., for example, 95% ethanol is a co-solvent having ethanol and water); and removing the solvent to obtain a powder composition comprising the sugar and the ED drug in a more soluble form. The embodiment contemplates a ratio of a sugar to an ED drug can be present in a weight ratio of about 1:1 to about 1:20 or from about 1 to about 10, and any value in between those ranges 1 to 20. For example, stevia can be used at a ratio of stevia to a compound of 3:1. In another embodiment, two sugars can be used to form a complex with the ED drug, such as a combination of rubusoside and stevioside in the presence of a poorly water-soluble compound and 95% ethanol (or another solvent). For example, the ED drug:rubusoside:stevioside could be in the ratio of 1.0:7.4:1.0. For a poorly water-soluble ED drug, the goal would be to keep the amount of the sugar below the GRAS (the FDA's Generally Regarded As Safe limits) recommended limit for each sugar. Another aspect contemplates the use of isopropyl alcohol as one of the solvents for use topically.

A method disclosed herein uses a solvent to dissolve the sugar and the compound or drug to create the hydrogen bonds and/or an inclusion complex capable of dissolving both the compound and the sugar. In one aspect, the solvent can be ethanol, methanol, water, hexane, or other pharmaceutically acceptable solvents or combinations thereof. In another aspect, the second solvent can be ethanol, methanol, water, hexane, or other pharmaceutically acceptable solvents.

In one embodiment, the complexes described herein can be represented by formula (I) as follows:

$$[DTG]_p Drug \qquad (I)$$

where DTG in formula (I) is a non-nutritive sugar as defined herein and a Drug is a PWS-ED drug and wherein p is the molar ratio of up to about 20 moles of the sugar (DTG) for each mole of said PSD, wherein the sugar is one or more of rubusoside, dulcoside A, dulcoside B, sucrose, D-fructose, sucralose, rebaudioside A, rebaudioside B, rebaudioside D, stevioside, stevia, n-octyl glucose, n-dodecyl-β-D-maltoside, Advantame®, neotame, thaumatin, saccharin, sucralose, a steviol glycoside, Lou Han Guo, aspartame, acesulfame potassium, or allulose, and provided that said water-soluble sugar-drug complex has at least a five (5) fold increase in the water solubility of said PWS-ED drug at 20° C. as compared to the water solubility of said drug not in said water-soluble sugar-drug complex. The p can be from about 1.0 to about 12.0, or from about 1.5 to about 10.0. The water-soluble complexes contemplated also include that the poorly water-soluble compound is a salt form of the compound. The complex may have been formed in the presence of an acid or a base. One embodiment disclosed is a method of improving a drug's solubility comprising: admixing (e.g., stirring) the drug with a sugar in a solvent; and removing the solvent to obtain a powder composition comprising the sugar and the drug in their more soluble form and/or complex. The embodiment contemplates that a drug and a sugar can be present in a weight ratio of about 0.1:1.0 to about 1.0:20.0 or from about 1.0 to about 10.0, and any 0.1 value in between those ranges 0.1 to 20.0. For example, stevia can be used at a ratio of stevia to drug of 3:1.

As defined below, DTGs as defined in formula (I) can be diterpene or triterpene glycosides or other non-nutritive sugars commercially available as a natural sweetener. Such DTGs include Stevioside and Rubusoside as well as other related compounds. An embodiment includes using a non-nutritive sugar in the disclosed method to bind through hydrogen bonds to a drug and/or in the form of a complex, wherein the sugar can be rubusoside, dulcoside A, dulcoside B, sucrose, D-fructose, sucralose, rebaudioside A, rebaudioside B, rebaudioside D, stevioside, stevia, n-octyl glucose, n-dodecyl-β-D-maltoside, Advantame®, neotame, thaumatin, saccharin, sucralose, a steviol glycoside, Lou Han Guo, aspartame, acesulfame potassium, or allulose.

A method disclosed herein uses a solvent or a co-solvent to dissolve the sugar and the PWS-ED drug. The solubility of both the sugar and the drug in the solvent or co-solvent used generates hydrogen bonding between and among these components. As the solvent or co-solvent is removed, the remaining hydrogen bonds are between the sugar and the drug which results in the complex having better water solubility than the compound in non-complexed form. In one aspect, the solvent can be ethanol, methanol, water, hexane, or another pharmaceutically acceptable solvent or mixtures thereof. Co-solvents can include water and an alcohol such as methanol, ethanol, or isopropanol. Higher-order solvent mixtures include, by way of example, water, methanol, and ethanol. The additional solvents can be ethanol, methanol, water, hexane, or a co-solvent, or another pharmaceutically acceptable solvent. Illustrative examples of cosolvents can include the following: about 50% to near just less than 100% solvent and water or about 50% to less than 100% ethanol with the remainder being methanol or 50% to less than 100% ethanol and up to about 50% to about 0.001% methanol and any value in methanol within that range. In another embodiment, instead of water, a buffer may be used.

Another embodiment contemplates a powdered formulation including lyophilized powders, produced by the methods disclosed, wherein the powdered formulation has improved solubility given the hydrogen bonding between the sugar and the drug forming a complex. This complex has improved water solubility as compared to the water solubility of the drug solubility characteristic prior to hydrogen bonding to a sugar. An embodiment contemplates that a sugar-drug complex formed by the method can have a weight ratio of drug to sugar of about 0.1:1.0 to about 1.0:20.0, or from about 1.0:1.0 to about 1.0:20.0 and any 0.1 value in between 0.1 to 1:20.0. Alternatively, the compound and the sugar are present in a mole ratio of about 1:1 to about 1:10 or in a mole ratio of 1:1 to 1:5 or in a mole ratio of 1:1 to 1:3 and any 0.01 value between each of these ratios provided herein.

In another embodiment, the complex can be formed with two disclosed sugars where the aggregate amount of the sugars used falls within the ratios discussed above. For example, a sugar-drug complex can be formed using rubusoside and stevioside as the sugars in a weight or mole ratio of 1:7.5 of rubusoside to stevioside and then combining this sugar mixture with a drug at a weight or mole ratio 8.5:1 of total sugars to the drug, or any in combination of disclosed sugars. In another example, both non-nutritive sugars are in a mole ratio of about 10.0:1.0 sugar to drug or 9.0:1, 8.0:1.0, 7.0:1.0, 6.0:1.0, 5.0:1.0, 4:0:1.0, 3.0:1.0, 2.0:1.0, or 1:1 and any 0.1 value in between. In another embodiment, the complex can be formed with a mixture of 3 or more sugars.

Another embodiment contemplates that the powdered formulation is suitable for reconstitution in water or saline, wherein the complex in the formulation allows for greater water solubility of the drug when complexed to the sugar than the drug has in the absence of sugar binding to the drug when reconstituted in water, saline, or buffered saline (e.g., phosphate buffered saline, PBS). The water, saline, and buffered saline can optionally be sterile. The reconstituted complex when formulated in sterile water or sterile saline can be administered to a subject in any appropriate form for administration such as intraperitoneally (ip), intranasally, intramuscularly (im), subcutaneously (sc), sublingually, orally, or buccally while oral delivery is preferred.

In the case of oral delivery, such includes sublingual formulations, the sugar-compound can be in the form of a tablet, a strip, a sublingual drop, a sublingual spray, a lozenge, or an effervescent buccal or sublingual tablet for rapid release such as drops, inhaled mist or powder, and nebulizer liquid. The powdered formulation can have a weight ratio of compound to sugar of about 1.0:1.0 to about 1.0:20.0, or from about 1.0:1.0 to about 1.0:10.0 and any 0.1 value between 0.1 to 1:20.0. Alternatively, the compound and the sugar are present in a mole ratio of about 1.0:1.0 to about 1.0:10.0 or any 0.01 value between. In another embodiment, the water-soluble complex comprises a molar ratio of about 2 to about 5 moles of the sugar for each mole of said poorly water-soluble drug.

The complexation of the drug with the DTG can be construed as a donor (DTG) receptor (drug) interaction, such as host-guest chemistry between the drug and a DTG. In effect, the complexation intertwines the PWS-ED drug with the sugar in the selected solvent, which essentially allows the drug to capture the water solubility of the sugar. Moreover, this captured solubility is retained in the upper portion of the gastrointestinal tract (GI) after ingestion. Upon passage into the lower part of the GI tract, the glucose molecules on the sugar are enzymatically cleaved in a time-dependent manner by endogenous bacteria to provide for the aglycon (diterpene or triterpene). See, for example, *Absorption and distribution of steviol glycosides in animal and human models*. Stevia Retrieved Technology. Jul. 31, 2023, from www.steviashantanu.com/single-post/2015/11/18/absorption-and-distribution-of-steviol-glycosides-in-animal-and-human-models. Without being limited to any theory, enzymatic cleavage of the sugar groups results in disaggregation (e.g., decomplexation) of the complex, which releases the poorly water-soluble drug. This process is sufficiently slow that substantial portions of an amount of the drug released at any given time can be absorbed.

Disclosed herein and contemplated is a water-soluble complex comprising a sugar and a poorly water-soluble ED drug, which complex comprises: a molar ratio of up to about 5 moles of the sugar for each mole of said poorly water-soluble drug, wherein the sugar can be for example one or more of rubusoside, dulcoside B, dodecyl-β-D-maltoside, stevioside, or rebaudioside A, provided that said water-soluble complex has at least a five (5) fold increase in the water solubility of said poorly water-soluble drug at 20° C. as compared to the water solubility of said drug, not in said water-soluble complex; and further provided that a maximum amount of the sugar in a daily unit dose of said complex is no more than about 10 mg/kg. The sugar used to make the water-soluble complex can be rubusoside.

Another water-soluble complex contemplates using the poorly water-soluble drug (i.e., erectile dysfunction drug) selected from the group consisting a free form, salt form, or polymorph of alprostadil, sildenafil, tadalafil, vardenafil, and avanafil. In the case of alprostadil, the complex increases the solubility to assist in transport of the drug across skin.

In another embodiment, the water-soluble complex can be a sugar selected from the group of rubusoside, rebaudioside A, dodecyl-β-D-maltoside, dulcoside B, or stevioside or any combination or permutation thereof.

In another embodiment, the water-soluble complex comprises a molar ratio of from about 2 to about 5 moles of the sugar for each mole of said poorly water-soluble drug.

In another embodiment, the water-soluble complex comprises a molar ratio of about 2 to about 4.5 moles of the sugar for each mole of said poorly water-soluble drug. In yet another embodiment, the water-soluble complex comprises a molar ratio of about 3 moles of the sugar for each mole of said poorly water-soluble drug. Another embodiment contemplates the water-soluble complex being stable when dissolved in water at pH 8.5 for at least about 2 hours.

In a further embodiment, the water-soluble complex is stable when dissolved in water at pH 4 for at least about 2 hours. In some cases, the water-soluble complex should be stable at a pH of about 1.5 to about 2.0 for at least 2 hours.

A further embodiment contemplates that the dried form of the water-soluble complex is stable at 30° C. for at least 90 days.

Another embodiment contemplates the water-soluble complex as in the form of a powder, a tablet, an orally disintegrating tablet, a chewable (e.g., a gummy) a capsule, a liquid, a gel, a thin film, a lozenge, an effervescent powder or tablet, an emulsion, or formulated for parenteral administration. Alternatively, the water-soluble complex can be a formulation prepared for parenteral administration to be administered topically, intradermally, intranasally, subcutaneously, or intramuscularly. A further embodiment contemplates the water-soluble complex formulated as a thin film, an effervescent powder or tablet, a syrup, a solution, an elixir, an emulsion, a chewing gum, a lollipop, a sublingual drop, a soft gel, or a tincture.

Another embodiment contemplates a water-soluble complex comprising a sugar and a poorly water-soluble drug, which water-soluble complex comprises: a molar ratio of about 3 moles of the sugar for each mole of said poorly water-soluble drug, wherein the sugar is one or more of rubusoside, rebaudioside A, dulcoside B, dodecyl-β-D-maltoside (DDM), or stevioside; wherein said water-soluble complex is stable in water at pH 8.5 and at pH 4.0 for at least 2 hours each (or in some cases, the water-soluble complex should be stable at a pH of about 1.5 to about 2.0 for at least 2 hours); provided that said water-soluble complex has at least a five (5) fold increase in the water solubility of said poorly water-soluble drug at 20° C. as compared to the water solubility of said poorly water-soluble drug not in the water-soluble complex; and further provided that a maximum amount of the sugar in a daily unit dose of said water-soluble complex is no more than about 280 mg.

Another aspect contemplates a method of making a water-soluble complex comprising a sugar and a poorly water-soluble drug, the method comprising the steps of admixing, in at least 85% ethanol, the sugar with the poorly water-soluble drug in a molar ratio of from about 2 to about 5 moles of the sugar for each mole of said poorly water-soluble drug until solubilized thereby forming the water-soluble complex, wherein the formation of the water-soluble complex can be determined by nuclear magnetic resonance spectroscopy, and wherein the sugar is one or more of rubusoside, rebaudioside A, dulcoside B, dodecyl-β-D-maltoside (DDM), or stevioside; and wherein the admixing step is optionally performed with a pharmaceutically acceptable acid; and optionally drying the water-soluble complex. A further method contemplates that the sugar used in the method is rubusoside or stevioside. The poorly water-soluble drug used in the method of making the water-soluble complex can be one or more of sildenafil, tadalafil, vardenafil, avanafil, alprostadil, or a pharmaceutically acceptable salt of any thereof. The method further can comprise drying the water-soluble complex to form a solid. The dried solid can be re-dissolved into a suitable liquid. In the case of alprostadil, the formulations of alprostadil and a sugar herein that are contemplated for complexation are for topical use only.

The method of preparing the water-soluble complex may further require the presence of a pharmaceutically acceptable acid, base, or buffer to be added in the admixing step in the presence of a sufficient amount of a pharmaceutically acceptable acid to solubilize and render the reaction mixture homogeneous and clear. The pharmaceutically acceptable acid to be used in the method can be acetic acid, ascorbic acid, aspartic acid, citric acid, formic acid, fumaric acid, gluconic acid, glutamic acid, glutaric acid, glycolic acid, hydrochloric acid, lactic acid, lauric acid, maleic acid, malic acid, malonic acid, nitric acid, oleic acid, oxalic acid, palmitic acid, propionic acid, salicylic acid, stearic acid, succinic acid, or tartaric acid.

The method of making the water-soluble complex can admix a molar ratio of from about 2 to about 5 moles of the sugar for each mole of said poorly water-soluble drug. The sugar can be rubusoside or stevioside. Alternatively, the water-soluble complex made by the method can have a molar ratio of about 2 to about 4.5 moles of the sugar for each mole of said poorly water-soluble drug. In another embodiment, the formed water-soluble complex from the method can comprise a molar ratio of about 3 moles of the sugar for each mole of said poorly water-soluble drug.

An exemplary method contemplates a method of drying the solubilized sugar(s) and poorly water-soluble compound to obtain a water-soluble sugar-drug complex, solubilizing the dried water-soluble sugar-drug complex in a second solvent, and filtering the solubilized water-soluble sugar-drug complex to provide for a clear aqueous solution of the complex.

These and other embodiments which will be apparent to those of skill in the art upon reading the specification provide the art with improvements in patient compliance, satisfaction, comfort, and overall treatment experience.

BRIEF DESCRIPTION OF THE FIGURES

FIG. 1 depicts the potential hydrogen bonding and/or inclusion complex formation between rubusoside and sildenafil (e.g., VIAGRA®). There is a total of 9 hydrogen intermolecular bonds possible between rubusoside and sildenafil (e.g., H—O; H—N; H—S; and NH—O). Sildenafil has an MW of 474.58 and an elemental analysis of C, 55.68; H, 6.37; N, 17.71; O, 13.48; and S, 6.76. Structures and the number of hydrogen bonds possible are based on original structure models and post-bonding NMR analysis.

DETAILED DESCRIPTION

Creating new means of enhancing the formation of water-soluble complexes of compounds having either poor water solubility or, for example, inadequate oral delivery due to unacceptable taste or consistency, has significant ramifications in many fields including pharmacology, animal care, food supplements, animal feed, and the like. The complexes formed using the methods herein can assist compounding pharmacies in formulating patient-specific amounts of an active compound as well as formulating the active compound into palatable formulations for any subject. Without being limited to any theory, the proposed sugar-drug combinations may be created by hydrogen bonding or by host-guest chemistry forming a complex, wherein two compounds are in a complex and one chemical compound has a cavity into which a "guest" compound can be accommodated. The interaction between the host and guest in a complex can include hydrophobic interactions such as van der Waals interactions. Nevertheless, in this sugar-compound form, the complex formed from the sugar-compound increases the compound's solubility in water over the compound alone. The complex also imparts a sweeter taste, instead of a bitter or acrid taste imparted by many compounds in free form or as salts. The sweeter taste will be of benefit when administering pharmaceuticals to patients by contributing the sweeter and more palatable taste.

The water-soluble sugar-ED drug complexes are also designed to improve the amount of drug delivered (Cmax) and/or the duration of a therapeutic amount of drug delivered over time. The underlying theory is that as the complex enters the large intestine, the release of the drug will be dependent on the presence of enzymes and/or conditions that degrade the sugars around the drug. Since the rate of entry of the complex into the large intestine will be slow and includes other materials as well and since the ratio of sugars to drug for each complex will likely be a Gaussian curve with some complexes having a higher ratio of sugar than others, the release rate would be prolonged enough that the amount of drug freed from the sugars and therefore available to transport to the liver extended over time. As the ratio of sugar to the complex drug increases, the duration of drug release should likewise increase. Using such complexes therefore permits the extended release which then correlates with inhibition of overloading of the drug relative to the transport mechanism which is likely what happens when the drug is administered as not part of a complex described herein. This, in turn, will provide for higher Cmax and longer duration of an efficacious concentration of the drug.

The following definitions provide guidance on term interpretation unless otherwise indicated by the context in which the term appears elsewhere in the specification.

By using a powdered or liquid formulation, dispensing proper doses is easier, reducing errors, variations, and waste based on variations in the pill-splitting technique. Another benefit achieved by the method and products produced by the method is a decreased amount of an active drug agent because with greater solubility there will be greater bioavailability. The method provides a cost-benefit of having to utilize fewer resources for less of an active compound but still achieving the desired patient outcome.

As used herein, the term "optional" or "optionally" means that the subsequently described event or circumstance may or may not occur and that the description includes instances where the event or circumstance occurs and instances where it does not.

As used herein, the term "about" when used before a numerical designation, e.g., temperature, time, amount, concentration, and such other, including a range, indicates approximations that may vary by (+) or (−) 15%, 10%, 5%, 1%, or any subrange and/or value therebetween. The term "about" when used concerning a dose amount means that the dose may vary by +/−10%. The term "about", when modifying the quantity (e.g., kg, L, or equivalents) of a substance or composition, the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through an inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of +1%, 2%, 3%, 4%, 5%, 10%, or 20%.

As used herein, the term "comprising" or "comprises" is intended to mean that the compositions or methods include the recited elements, but do not exclude others.

As used herein, the term "consisting essentially of" when used to define compositions and methods, shall mean excluding other elements of any essential significance to the combination for the stated purpose. Thus, a composition consisting essentially of the elements as defined herein, or a method consisting essentially of the steps as defined herein, would not exclude other materials that do not materially affect the basic and novel characteristic(s) of the claimed subject matter.

As used herein, the term "consisting of" shall mean excluding more than trace elements of other ingredients or substantial method steps. Embodiments defined by each of these transition terms are within the scope of this disclosure.

The "weight ratio" of a "sugar to a compound" in a formulation may range from about 0.1:1, 1:1, 2:1, 3:1, 4:1, 5:1, 6:1, 7:1, 8:1, 9:1, 10:1, and 20.0:1.0, and any 0.1 value between. Alternatively, the ratio can be about 1.0:0.001 and about 20.0:1.0.

The "mole ratio" or "molar ratio" of a sugar to a compound can range from 1.0 to 0.001 or 10.00 to 0.1 and any 0.01 value between those two ranges. The "molar ratio" of a "sugar to a drug compound" in a formulation may range from about 1:1, 2:1, 3:1, 4:1, 5:1, 6:1, 7:1, 8:1, 9:1, or to about 10:1 and up to about 20:1 and any 0.1 value between. Alternatively, the sugar to drug compound ratio can be about 1.00:1.00 to about 5.00:1.00, and any 0.01 value within that range. In one embodiment, an about 2.0 to about 1.0 molar ratio of sugar to PSD is used.

The use of the term "sugar" means that the sugar is a non-nutritive sweetener. A sugar or "DTG" as used herein can be rubusoside, dulcoside B (also known as rebaudioside C), stevia, rebaudioside A (also known as stevioside A3), stevioside (also known as diterpene glycoside and has a chemical formula of C38H60O18), n-octyl glucose, n-dodecyl-β-D-maltoside (also known as dodecyl maltoside or lauryl maltoside), stevia (has a chemical formula of C44H70O23), and a steviol glycoside such as that derived from *Stevia rebaudiana*. While other stevia-like sugars are known, only those that are FDA GRAS-approved are contemplated. Preferably, the sugar is one or more of rubusoside, stevia, dulcoside B, stevioside, n-dodecyl-β-D-maltoside, or rebaudioside A which can be used in any combination or permutation. Also contemplated is any permutation of the listed 6 sugars (2 of the sugars, 3 of the sugars, etc.). The price of the sugar is also a factor in whether a sugar is commercially a good sugar for solubilizing a poorly water-soluble or insoluble drug.

By a "ED compound", a "ED drug-compound", a "poorly water-soluble ED compound", or a "PWS-ED drug" is meant an ED drug compound, wherein the drug compound is poorly water-soluble or insoluble (e.g., a poorly water-soluble drug, PSD, also includes a poorly water-soluble compound). A "poorly water-soluble ED drug or compound" is a compound that because of its inadequate aqueous solubility either lacks or compromises its commercial utility. The compromised commercial utility includes art recognized as deficient in solubility as evidenced by attempts to improve solubility including without limitation use of nanotechnology, the use of prodrugs, the use of a non-aqueous solvent delivery, and the like. The term "insoluble" is often applied in the art to poorly or very poorly water-soluble compounds (see e.g., Savjani et al. "Drug Solubility: Importance and Enhancement Techniques," ISRN Pharm. 2012, doi: 10.5402/2012/195727). Generally, a poorly water-soluble compound is considered "poorly soluble" in water at 20° C. when less than about 1 mg/mL of the compound is made soluble over the physiological pH range (see e.g., C. Moreton, "Poor Solubility—Where do we stand 25 years after the 'Rule of Five'?" Amer. Pharm. Rev. (2021). While not being bound by theory, the drug compound preferably has available hydrogen bonding sites to form such bonds with a sugar and/or for the compound and the sugar to form a complex. The exemplary drugs mentioned herein also are intended to include their salt forms, their polymorphs, their free forms, or metabolites or precursors (pro-drug) thereof. By a "compound" or "drug-compound" or "poorly soluble drug" is a drug compound, wherein the drug compound is poorly soluble or insoluble in water (e.g., a poorly soluble drug, PSD). While not being bound by theory, the drug compound preferably has available hydrogen bonding sites to form such bonds with a sugar and/or for the compound and the sugar to form a complex. For the compounds and methods described herein, the PSD is a erectile dysfunction drug such as sildenafil (or desmethyl sildenafil) or its salt sildenafil citrate (SLC), which is sold under the brand names Viagra® and Revatio® or other pharmaceutically acceptable salt (e.g., lactate or nitrate), tadalafil or its pharmaceutically acceptable salt (sold under the brand names Cialis® and Adcirca) or crystal forms such as those described in US Pub. 2006111571, vardenafil or its pharmaceutically acceptable salt (vardenafil HCl, under brand names Levitra® or Staxyn®) or other salt form (e.g., anhydrous hydrochloride, hydrochloride trihydrate, hydrochloride), and avanafil or pharmaceutically acceptable salt (under the brand name Stendra®). The properties of the drugs are provided in the Table below:

method of improving a drug/compound's solubility is that the storage stability of the sugar-compound can be increased. For example, the complex formed by the described methods produces a sugar-compound complex that is stable when dissolved in water at a pH of 8.5 for at least about 2 hours. Additionally or alternatively, the water-soluble sugar-drug complex is stable when dissolved in water at pH 4 for at least about 2 hours, and in some instances at a pH of about 1.4 to 1.6 for at least about 2 hours. Additionally or alternatively, the dried form of the water-soluble complex is stable at 30° C. for at least 90 days. Additionally or alternatively, the complex formed by the described methods forms a dried complex that does not require refrigeration and is stable at room temperature for at

TABLE

| PSD Compound Name<br>IUPAC Name | Solubility | Molecular<br>Formula | Molecular<br>Weight |
|---|---|---|---|
| Avanafil<br>4-[(3-chloro-4-methoxyphenyl)methylamino]-2-[(2S)-2-(hydroxymethyl)pyrrolidin-1-yl]-N-(pyrimidin-2-ylmethyl)pyrimidine-5-carboxamide | Soluble in DMSO (97 mg/ml at 25° C.); methanol, water (<1 mg/ml at 25° C.), and ethanol (<1 mg/ml at 25° C.) | $C_{23}H_{26}ClN_7O_3$ | 483.9 g/mol |
| Sildenafil<br>5-[2-ethoxy-5-(4-methylpiperazin-1-yl)sulfonylphenyl]-1-methyl-3-propyl-6H-pyrazolo[4,3-d]pyrimidin-7-one | solubility in water: 3.5 mg/mL as sildenafil citrate | $C_{22}H_{30}N_6O_4S$ | 474.6 g/mol |
| Tadalafil<br>(2R,8R)-2-(1,3-benzodioxol-5-yl)-6-methyl-3,6,17-triazatetracyclo[8.7.0.0$^{3,\,8}$.0$^{11,\,16}$]heptadeca-1(10),11,13,15-tetraene-4,7-dione | 220 mg/L at 25° C. in water | $C_{22}H_{19}N_3O_4$ | 389.4 g/mol |
| Vardenafil<br>2-[2-ethoxy-5-(4-ethylpiperazin-1-yl)sulfonylphenyl]-5-methyl-7-propyl-3H-imidazo[5,1-f][1,2,4]triazin-4-one | 3.5 mg/L at 25° C./<br>Estimated/in water | $C_{23}H_{32}N_6O_4S$ | 488.6 g/mol |
| Alprostadil | 8000 µg per 100 mL distilled water; it is nearly insoluble in ethanol, ether and ethyl acetate. | $C_{20}H_{34}O_5$ | 354.481 g/mol |

A poorly water-soluble drug is a compound that can dissolve at no more than about 100 µg/mL at 20-25° C. Moderately soluble drugs (have a solubility of less than 10 mg/mL) are those wherein less than 10 mg of the compound can dissolve in water and preferably less than 5 mg of the compound can dissolve in a milliliter of water. In the case of sildenafil, which is moderately water soluble, a complex can be formed between it and a sugar described herein for the purpose of enhancing topical transport across the skin barrier. In the case of alprostadil, a poorly water-soluble ED drug, an increase in water solubility can improve transport across the skin barrier.

A "stable" sugar-ED compound is a water-soluble complex (i.e., [DTG]$_p$Drug) prepared by the methods described herein that can be prepared and isolated and whose structure and properties remain or can be caused to remain essentially unchanged for a period of time sufficient to allow the use of the compound for the purposes described herein (e.g., therapeutic administration to a subject). As noted elsewhere, the DTG can also be substituted by one of the other sugars listed herein. Another characteristic that may be imparted by the least 24 hours. The water-soluble complex formed by the methods described herein is sought to have at least a five (5) fold increase in the water solubility of said poorly water-soluble drug at 20° C. as compared to the water solubility of said poorly water-soluble drug not in the water-soluble complex; and further provided that a maximum amount of the sugar in a daily unit dose of said water-soluble complex is no more than about 280 mg.

The method is dissolving a compound in ethanol in the presence of a sugar, followed by drying or evaporating (e.g., freeze-drying or lyophilizing or other means of evaporating the ethanol from the mixture) the liquid from the composition. Lyophilizing generally requires pre-freezing of the complex followed by primary and secondary drying steps. The remaining residue comprising the hydrogen-bonded and/or sugar-compound complex can then be formulated into a solid form for oral, sublingual, or buccal administration such as a pill, capsule, a caplet, a chewable (e.g., a gummy or gum), tablet, a lozenge, and a soft gel. The water-soluble drug complex (e.g., hydrogen-bonded and/or inclusion complexed sugar-compound) can also, or alternatively, be formulated into a suppository, lotion, gel, and/or ointment. The water-soluble drug complex can also be formulated as an inhalable powder. The water-soluble complex can be formulated into a suitable topical form. In another aspect, the water-soluble complex can be formulated into an injectable liquid for injection into a subject topically, via inhalation, subcutaneously (SC) or administered as a patch or in the form of a hydrogel, intraperitoneal (IP), and intramuscularly (IM). For example, sildenafil citrate has been formulated as a microemulsion-loaded hydrogel as a means of delivering sildenafil to the penis and its local cellular metabolic mechanism. In one example, sildenafil citrate was formulated as a microemulsion system using isopropyl myristate, Tween 80, PEG400, and water (30:20:40:10); the hydrogel used in the microemulsion was 2% w/w poloxamer 188 (Atipairin et al., "Development of a sildenafil citrate microemulsion-loaded hydrogel as a potential system for drug delivery to the penis and its cellular metabolic mechanism," Pharmaceutics 12(11): 1055 (2020)). Alternatively, a transdermal patch can be made using nanotechnology to deliver sildenafil. Delivery can be performed when combined with transdermal enhancers (see e.g., WO2014152382). Sildenafil has also been formulated as a cream at 3.6%. It is contemplated herein to use a surfactant such as a poloxamer (e.g., P188), T20, or T80 to assist in solubilizing the sugar and the PSD. The surfactant can be used alone with the sugar and PSD or in further combination with a pharmaceutically acceptable solvent, acid, base or buffer or a combination thereof.

Alternatively, the lyophilized water-soluble complex can be formulated into a liquid formulation for administration such as for use in a metered nasal spray, inhaled mist, eye drop, or nebulized by a patient. Additionally, or alternatively, a lyophilized water-soluble aggregate can be formulated as a food additive or as an additive into an animal feed. The PSD must be one that can be solubilized fully or partially in either 95% ethanol, an aqueous ethanol solution of 50% ethanol or greater (e.g., 50%, 55%, 60%, 70%, 80%, 85% 90%, 91%, 92%, 93%, 94%, and 95% spectrophotometric grade ethanol) in the presence of a sugar. Preferably, the PWS-ED drug and sugar optionally having the pharmaceutically acceptable acid is solubilized in at least about 85% ethanol. Optionally, the water-soluble aggregate remains soluble without the formation of a precipitate for at least 24 hours after formation.

If desired, a polyethylene glycol (PEG) can be optionally added to the liquid and powdered formulations to further improve bioavailability. Typically, this is between 2000 and 6000 Daltons, between 3000 and 4500, or between 3200 and 3700 as well as other pharmaceutically acceptable molecular weights utilized when formulating PEG with a chemical compound. Popular commercially available PEG forms have a molecular weight of 3350, 4000, and 6000 Daltons. The preparation of PEG may be polydisperse or monodisperse, for example. If polydisperse, then the molecular weight describes the weighted average molecular weight of the preparation. According to the formulations in powder or liquid form, the weight ratio of PEG to a compound may range between and including 5:1, 6:1, 7:1, 8:1, 9:1, and 10:1. In one embodiment, the weight ratio is about 8:1.

For administration, the powdered form may be reconstituted in a liquid vehicle, either at the point of manufacture, at the dispensing pharmacy, or by the patient. The liquid vehicle may be water, a buffered aqueous solution, a syrup, or an aqueous beverage, such as an energy drink or an electrolyte-rich drink. For example, the sugar-compound having improved solubility can be reformulated for example into sterile saline, or another sterile liquid carrier for administration to a subject as an eye drop or via subcutaneous (s.c.), intranasally, intraperitoneal (i.p.), intramuscular (i.m.), or oral routes (oral to enter the gastrointestinal tract or for buccal or sublingual administration). The sugar-compound can also be formulated into a metered nasal spray or delivered by subcutaneous or intramuscular injection.

For certain poorly water-soluble compounds, the use of a surfactant (e.g., Tween such as T20, T60, T80, T85, or a Poloxamer, such as P188 and P407 can be used) may be needed to enhance solubilization of the one or more sugars and the compound in a solvent or solvent mixture. Any surfactant for use in such a fashion must be capable of having surface and interfacial tension measurements.

Suitable ingredients for formulating a tablet or pill or another solid oral form of the water-soluble aggregate may include any or all of, for example, corn starch, magnesium stearate, microcrystalline cellulose, povidone, sodium lauryl sulfate, polyethylene glycol, titanium dioxide, and hypromellose. Additional compositions incorporating the described complexes can include formers, oral stool softeners, oral stimulants, and/or rectal suppositories.

While the dissolution of the water-soluble aggregate is slow enough to allow for the drug to move into the small intestine without precipitating in the stomach, additional means of extending drug release are known, such as enteric coated tablets, additionally coating the aggregates with a slowly dissolving polymer wherein the polymer can be selected by a desired length and/or thickness that can vary the drug release rate, placing the aggregate in a gelative capsule, placing the aggregate into an insoluble matrix (e.g., Slow-K or Imdur Durules), placing the aggregate into an eroding matrix (e.g., MST Continus, Phyllocontin Continus), and/or enclosing the aggregate in a semi-permeable membrane. See, e.g., June 2011 "Pharmaceutical Issues when Crushing, Opening or Splitting Oral Dosage Forms," by the Royal Pharmaceutical Society. Additional modified-release oral dosage forms include: "extended-release drug products" wherein a dosage form of the aggregate allows at least a twofold reduction in dosage frequency as compared to that drug aggregate being presented without the extended-release format. Examples of extended-release dosage forms include controlled-release, sustained-release, and/or long-acting drug products. Another modified-release oral dosage is a delayed-release drug product. In the delayed release form, the aggregate dosage form releases a discrete portion or discrete portions of the drug aggregate at a given time other than promptly after administration. Enteric-coated dosage forms are common delayed-release products (e.g., enteric-coated aspirin and other NSAID products). Another modified-release oral form of the aggregate contemplated is a targeted-release drug product. An aggregate dosage form that releases the complex at and/or near the intended physiologic site of action. Another modified-release oral dosage of the aggregate is orally disintegrating tablets (ODT) or equivalent. ODT has been developed to disintegrate rapidly in the saliva after oral administration. An ODT form of the complex may be used without the addition of water. The water-soluble aggregate is dispersed in saliva and swallowed with little or no water.

As used herein, a "sugar-compound" or a "hydrogen-bonded sugar-compound" are the same and are formed using the disclosed method. Without being bound by theory, the sugar-compound can have hydrogen-bonds created between the sugar and the compound forming a complex. In all instances wherein "sugar-compound" is used it is to be interpreted as inclusive of hydrogen-bonds and/or in the form of a complex through van der Waals bonding. The use of the term "sugar" means that the sugar is a non-nutritive sweetener. A non-nutritive sweetener sugar or "DTG" as used herein can be rubusoside, dulcoside B (also known as rebaudioside C), stevia, rebaudioside A (also known as stevioside A3), stevioside (has a chemical formula of C38H60018), n-octyl glucose, n-dodecyl-β-D-maltoside (also known as dodecyl maltoside or lauryl maltoside), stevia (has a chemical formula of C44H70023), and a steviol glycoside such as that derived from *Stevia rebaudiana*. While other stevia-like sugars are known, only those that are FDA GRAS-approved are contemplated. Preferably, the sugar is one or more of rubusoside, stevia, dulcoside B, stevioside, n-dodecyl-β-D-maltoside, or rebaudioside A which can be used in any combination or permutation. Also contemplated is any permutation of the listed 6 sugars (2 of the sugars, 3 of the sugars, etc.). The price of the sugar is also a factor in whether a sugar is commercially a good sugar for solubilizing a poorly water-soluble or insoluble drug. Exemplary sugars for making the "sugar-compound" are rubusoside, dulcoside A, dulcoside B, sucrose, D-fructose, sucralose, rebaudioside A, rebaudioside B, rebaudioside D, stevioside, stevia n-octyl glucose, or n-dodecyl-β-D-maltoside, with the proviso that when the sugar is rubusoside the compound is not praziquantel. The exemplary sugars are diterpene diglycosides (DTGs) and triterpene glycosides. Not to being bound by a theory, it is believed that upon aggregation (e.g., complexation) of the DTG with the PSD, a stable aggregate (e.g., complex) occurs, presumably by non-covalent hydrogen bonding and optionally hydrophobic-hydrophobic interactions, such as van der Waal forces. The use of the term "sugar" as used herein is a non-nutritive sweetener. A sugar as used herein can be dulcoside A, sucrose, D-fructose, sucralose, a rebaudioside B, rebaudioside D, stevia, n-octyl glucose, Advantame®, Neotame®, thaumatin, saccharin, Lou Han Guo, aspartame, acesulfame potassium (Ace-K), allulose, rubusoside, dulcoside B (also known as rebaudioside C), rebaudioside A (also known as stevioside A3), a stevioside, n-octyl glucose, and a steviol glycoside such as that derived from *Stevia rebaudiana*. While other stevia-like sugars are known, only those that are FDA GRAS-approved or approved for use in Europe are contemplated. Preferably, the sugar is one or more of rubusoside, stevia, dulcoside B, stevioside, or rebaudioside A which can be used in any combination or permutation. Also contemplated is any permutation of the listed 6 sugars (2 of the sugars, 3 of the sugars, etc.). The price of the sugar is also a factor in whether a sugar is commercially a good sugar for solubilizing a poorly water-soluble or insoluble drug. Additional contemplated sugars that are not DTG sugars but can be paired with a PSD as described herein include:

Advantame®—is an aspartame analog; N—[N-[3-(3-hydroxy-4-methoxyphenyl) propyl]-α-aspartyl]-L-phenylalanine-1-methyl ester (Otabe et al., "Advantame®—An Overview of Toxicity Data," *Food and Chemical Toxicity* 49(S1): S2-S7, 2011. Advantame® has a low glycemic index (GI) and zero calories but can cause a spike in insulin.

Neotame®—tradename is Newtame® and is a derivative of aspartame that is classified as an aspartyl-derived dipeptide. Neotame® has a low glycemic index (GI) and zero calories but can cause a spike in insulin.

Thaumatin—is also known as TALIN®, Soma sweet. It is a mixture of the sweet proteins thaumatin I and thaumatin II derived from *Thaumatococcus danielli*.

Saccharin—is also known as saccharine or benzosulfimide and in such salt forms as saccharin sodium and saccharin calcium. It is sold under the brand names Sweet and Low®, Sweet Twin®, Sweet'N Low® and Necta Sweet®. Saccharin has a low glycemic index (GI) and zero calories but can cause a spike in insulin.

Sucralose—sold under the name Splenda and is an organochlorine sweetener having the chemical name of 1,6-dichloro-1,6-dideoxy-β-D-fructofuranosyl-4-chloro-4-deoxy-α-D-galactopyranoside (Schiffman et al., "Sucralose, A Synthetic Organochlorine Sweetener: Overview of Biological Issues," *J. Toxicol Environ. Health B. Crit. Rev.* 16(7): 399-451, 2013). Sucralose has a low glycemic index (GI) and zero calories but can cause a spike in insulin.

Lou Han Guo—also goes by the name of *Siraitia grosvenorri*, swingle fruit, monk fruit, and luohan guo from which sweeteners can be derived that have no calories. The FDA has called this Swingle Fruit Extract (SGFE). The compounds that give the sweetness are mogrosides, which have a mogrol backbone and glucose units (glycosides) attached to it. They may be sold under the brands Monk Fruit in the Raw®, Lakanto®, PureLo®, SPLENDA® Monk Fruit Sweetener, SweetLeaf®, and Whole Earth®. SGFE does not appear to raise blood sugar levels.

Aspartame—is sold under the names Nutrasweet, Equal, and Sugar Twin and does contain calories. The chemical name is L-aspartyl-L-phenylalanine methyl ester. It is a dipeptide composed of phenylalanine and aspartic acid. Aspartame has a low glycemic index (GI) and zero calories but can cause a spike in insulin.

Acesulfame potassium—is also known as Ace-K and is sold under the brand names Sweet One® and Sunett®. Ace-K has a low glycemic index (GI) and zero calories but can cause a spike in insulin.

Allulose—is a sugar that naturally occurs in figs and raisins. It is also known as D-psicose or D-allulose and has few calories. It does not impact insulin or blood sugar levels. Tani et al., "Allulose for the attenuation of postprandial blood glucose levels in healthy humans: A systematic review and meta-analysis," *PLOS One* 18(4): e0281150, 2023.

The sweetness of a sugar is compared to table sugar (sucrose) and is summarized in the following table obtained from the US FDA:

| Sugar | Times Sweeter than Sucrose |
| --- | --- |
| Advantame ® | 20,000 |
| Neotame ® | 7,000-13,000 |
| Thaumatin | 2,000-3,000 |
| Saccharin | 200-700 |
| Sucralose | 600 |
| Steviol Glycosides | 200-400 |
| Luo Han Guo | 200-250 |
| Aspartame | 200 |
| Acesulfame Potassium (Ace-K) | 200 |

A "stable" sugar-compound is a water-soluble complex (i.e., [DTG]» Drug) prepared by the methods described herein that can be prepared and isolated and whose structure and properties remain or can be caused to remain essentially unchanged for a period of time sufficient to allow the use of the compound for the purposes described herein (e.g., therapeutic administration to a subject).

Any of the components can be packaged in a kit, either separately in individual vessels, or in admixtures with each other. The end user may reconstitute the components with an included diluent or with a diluent of her choosing. The kit, in addition to the components, either separately or in mixtures, may contain instructions for use, tools for mixing and/or administering, storage vessels, etc.

The terms "patient" and "subject" include an animal patient or animal subject, but is preferably human. Patients and subjects that can be treated with a complex or composition comprising a described complex as disclosed herein. A suitable patient can be a human man who having a condition resulting in erectile dysfunction.

The term "pharmaceutically acceptable salt" refers to a salt (including an inner salt such as a zwitterion) that possesses effectiveness similar to the parent compound and which is not biologically or otherwise undesirable (e.g., is neither toxic nor otherwise deleterious to the recipient thereof). The term "salt(s)", as employed herein, denotes any of the following: acidic salts formed with inorganic and/or organic acids, as well as basic salts formed with inorganic and/or organic bases. However, the compositions/compounds described herein are sugar forms of a drug compound. The drug or compound to be complexed with a sugar can be in a salt form of a drug or compound or the pure form of the compound. A drug salt form can allow for the salt component to occupy a binding site for a sugar, so if a compound lacks adequate bonding sites, it can be important to use a salt free form to form the complex. By "a pharmaceutically acceptable salt" is meant a salt used in a medicine that is approved by the U.S. FDA or the European Medicines Agency (EMA). The use of a pharmaceutically acceptable salt as used in the methods described herein is to improve the solubility of the sugar and insoluble drug.

"Pharmaceutically acceptable acids" for use in solubilizing the compounds include 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; hydrobromic acid; hydrochloric acid; isobutyric acid; tartaric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid. Sec e.g., P. H. Stahl and C. G. Wermuth, editors, Handbook of Pharmaceutical Salts Weinheim/Zürich: Wiley-VCH/VHCA, 2002.

Examples of bases including pharmaceutically acceptable bases include sodium hydroxide, zinc hydroxide, calcium carbonate, potassium hydroxide, lithium hydroxide, rubidium hydroxide, magnesium hydroxide, barium hydroxide, calcium hydroxide, strontium hydroxide, and potassium oxide. Other bases include trimethylamine, methylamine, aniline, and pyridine. Buffers can also be used instead of an acid or base to solubilize the compound and sugar. Exemplary buffers include a bicarbonate solution, a carbonate solution, and sodium phosphate (pKa 2.1, 7.2, and 12.3).

For embodiments of the method described herein to solubilize a compound or sugar, the temperature of the compound, sugar, and solute can range from about 15° C. to about 60° C., generally about 5° C. to about 10° C. from room temperature. An exemplary range is between about 20 and 35° C. or about 20 to 30° C.

By the phrase "a pharmaceutically acceptable composition" is meant a composition comprising the water-soluble complex formed from a sugar and an erectile dysfunction drug and one or more of a carrier, excipient (e.g., gelatin, cellulose, cellulose derivatives, polyvinylpyrrolidone, a starch, sucrose, and PEG), stabilizer (e.g., glycine, vitamin E, carboxymethylcellulose, sodium lauryl sulfate), a thickener, and a further sweetener. The composition can be a solid or a liquid form.

By "improved solubility" of a compound is meant an improvement of a compound's solubility in water absent the addition of a sugar after the method of dissolving the compound in the presence of a sugar in ethanol or aqueous ethanol. After solubilizing the sugar and the compound in ethanol or aqueous ethanol, the ethanol is evaporated for example under a high rotary vacuum. The powder resulting from the evaporation step is then resolubilized (dissolved) in water. Another solvent can be methanol at 80% methanol, 95% (ACS grade) or greater (to 100% methanol) as well as combinations of methanol and ethanol or methanol and water. After solubilizing the sugar and the compound in ethanol or aqueous ethanol, the ethanol is evaporated for example under a high rotary vacuum. The powder resulting from the evaporation step is then resolubilized (dissolved) in water. As above, improvements in water solubility are measured at about 20° C.

By the terms "water-soluble complex", "water-soluble drug complex", "water-soluble sugar-drug complex", and "water-soluble sugar-ED drug complex" is meant to include a sugar (e.g., rubusoside, stevia, dulcoside B, stevioside, n-dodecyl-β-D-maltoside, rebaudioside A or other indicated sugar discussed herein) in a complex with a poorly water-soluble erectile dysfunction drug as discussed herein. A described method of obtaining such an ED drug-sugar complex can be via dissolution with absolute ethanol (100%) or 95% ethanol optionally with a pharmaceutically acceptable acid forms a complex, and optionally further having been solubilized in the presence of a pharmaceutically acceptable acid, base or buffer. The compound or drug can be any free form of an ED drug or its salt, hydrate, or polymorph, or a salt that can be solubilized fully or partially in either 95% ethanol or 100% ethanol (absolute ethanol), an aqueous ethanol solution of 50% ethanol or methanol or greater (50%, 55%, 60%, 70%, 80%, 85% 90%, 91%, 92%, 93%, 94%, 95% spectrophotometric grade ethanol or absolute ethanol) in the presence of a sugar. The solubilized sugar and ED drug have the ethanol removed and the powder can then be resolubilized in water to a greater degree than the drug when not in the form of a complex. Optionally, the hydrogen-bonded complexed sugar-compound can be assessed for up to 24 hours after solubilization for stability to remain soluble. The term "aggregate" as used herein is meant to include aggregation or complexation, wherein complexation can further include multiple complexes that form an aggregate. The compound can be the salt form, acid form, or base form of the compound. The method of improving the water solubility of a compound involves taking the compound and dissolving it in about 70% to 95% ethanol in the presence of a sugar. The compound-to-sugar weight ratio can be from about 0.1:1.0 to about 1.0:1.0, from about 1.0:1.0 to about 1.0:10.0 or 1.0:20.0, and any 0.1 value between about 0.1 to about 20.0.

By "daily unit dose" is meant the total amount of a compound given daily to a subject, whether in one administration or over multiple administrations and, when one administration is used, whether one or multiple pills, capsules, tablets, or other formulations are used. A dosage of a formulation comprising the compound (e.g., as the water-soluble complex) would contain no more than a Generally Recognized as Safe (GRAS) amount of any constituent of the formulation. For example, in the case of a steviol sugar used as the DTG, a dosage would provide no more than about 10 mg/kg of the steviol sugar, because more than that for an average male of 70 kg, would result in a dosage of about 700 mg of the sugar administered in one dosage. In another embodiment, the dosage would provide no more than 5.0 mg/kg of the steviol sugar (or other non-nutritive sugar) to the subject. Also contemplated are about 2.0 mg/kg, 3.0 mg/kg, 4.0 mg/kg and 6.0 mg/kg amount of steviol sugar per dosage.

Another characteristic that may be imparted by the method of improving a drug/compound's solubility by hydrogen bonding the drug/compound to a sugar is that the storage stability of the sugar-compound can be increased.

The water-soluble sugar-drug complex may be mixed with other pharmaceutically acceptable excipients that are pharmaceutically acceptable and are compatible with the active ingredient in the drug. Suitable pharmaceutically acceptable excipients include water, saline, dextrose, glycerol, and ethanol, or combinations thereof. Intravenous vehicles for use in delivering the water-soluble complex include fluid and nutrient replenishers, electrolyte replenishers, such as those based on Ringer's dextrose, and the like. Aqueous carriers for use in a liquid formulation containing the water-soluble complex include water, alcoholic/aqueous solutions, emulsions, or suspensions, including saline or buffered media. A pharmaceutically acceptable carrier for parenteral administration includes sterile, aqueous, or non-aqueous solutions, suspensions, and emulsions. Aqueous parenteral vehicles for delivering the water-soluble complex include sodium chloride solution, Ringer's dextrose, dextrose and sodium chloride, lactated Ringer's, or fixed oils.

The water-soluble complex may be mixed with other pharmaceutically acceptable excipients that are pharmaceutically acceptable and are compatible with the active ingredient in the drug. Suitable pharmaceutically acceptable excipients include water, saline, dextrose, glycerol, and ethanol, or combinations thereof.

Stable complexes of this disclosure optionally have the formulae of formula (I) and (II) as described in the methods described herein. The stable complexes that can be prepared and isolated and whose structure and properties remain or can be caused to remain essentially unchanged for a period of time sufficient to allow the use of the compound for the purposes described herein (e.g., therapeutic administration to a subject). As noted elsewhere, the DTG can also be substituted by one of the other sugars listed herein. Another characteristic that may be imparted by the method of improving a drug/compound's water solubility is that the storage stability of the sugar-compound can be increased. For example, the sugar-drug complex formed by the described methods produces a sugar-compound complex that is stable when dissolved in water at a pH of 8.5 for at least about 2 hours. Additionally or alternatively, the water-soluble sugar-drug complex is stable when dissolved in water at pH 4 for at least about 2 hours, or in some cases at a pH of at least about 1.4 to 1.5 to 1.6 for at least about 2 hours. Additionally, or alternatively, the dried form of the water-soluble sugar-drug complex is stable at 30° C. for at least 90 days. Additionally or alternatively, the sugar-drug complex formed by the described methods forms a dried complex that does not require refrigeration and is stable at room temperature for at least 24 hours. The water-soluble sugar-drug complex formed by the methods described herein is sought to have at least a five (5) fold increase in the water solubility of said poorly water-soluble drug at 20° C. as compared to the water solubility of said poorly water-soluble drug not in the water-soluble sugar-drug complex; and further provided that a maximum amount of the sugar in a daily unit dose of said water-soluble sugar-drug complex is no more than about 280 mg.

The water-soluble complex can optionally include a preservative and/or an additive. Preservatives and additives contemplated for use with the water-soluble complex can include antimicrobials, anti-oxidants, chelating agents, inert gases, and the like. The preservative and/or additive is admixed with the water-soluble complex after the formation of the complex.

By the phrase "poorly water-soluble ED drug", "PSD", "PWS-ED drug" or "drug compound" is meant an ED drug candidate or a regulatory authority-approved ED drug that has a water solubility when used alone of no more than 10 mg/mL in distilled water. A regulatory authority-approved drug can be a drug approved by the U.S. FDA and/or EMA or other foreign drug regulatory body. The compounds can be in their free form, a salt form or as a polymorph.

Another characteristic that may be imparted by the method of improving a drug/compound's solubility is that the storage stability of the sugar-compound can be increased.

The above disclosure generally describes the materials and methods for making compounds such as drugs more soluble through sugars. The scientific principles behind the chemical interactions of a sugar compound and a drug compound discussed herein. A more complete understanding can be obtained by reference to the following specific examples which are provided herein for purposes of illustration only, and are not intended to limit the scope of the methods and compositions described herein. The amounts of a sugar (DTG) used in the examples are also amounts that can be claimed and should not be excluded from claiming merely because the amount is cited in an example.

In all the following examples, the same conditions were used unless otherwise noted. The water used is deionized, distilled water. Unless indicated otherwise, 95% ethanol (ACS spectrophotometric grade, unless otherwise specified) was used. In all cases, high vacuum drying was performed at room temperature. All examples used an Edvards Model RV8 high vacuum pump with an IKA model C-mag HS7 magnetic stirrer. The rotary evaporator used was a Heidolph Basis Hei-VAP value (No. 560-00000-01-1). The reagents used were as follows:

| Compound Name | CAS # | Purity % | Source |
|---|---|---|---|
| Sildenafil | 139755-83-2 | 95% | Combi Blocks |
| Stevioside | 57817-89-7 | 95+% | Ambeed |
| Rebaudioside A | 58543-16-1 | 98+% | Ambeed |
| Dulcoside B | N/A | 95+% | Matrix Scientific |
| Rubusoside | | 98+% | China |
| N-octyl glucose | 29836-26-8 | | CCN Industries Ltd. |

EXAMPLE 1—Praziquantel and Stevioside

While praziquantel is not an erectile dysfunction drug as claimed, the complex formed with a DTG exemplifies the combination and ability to improve the solubility of a PSD. Additional examples are provided to reflect the impact of molar ratios, and different non-nutritive sugars for use to make a complex using different solvents.

Generally, ingredients are deposited into a sealed container with ethanol and vortex-mixed to form a solution. The solution is subjected to centrifugation. The ethanol is evaporated off and the dried mixture was dissolved in water. This mixture is centrifuged again and the supernatant is filtered through a membrane. The flow-through is dried forming the compounded praziquantel. In one embodiment, the admixing process involves dissolving the PSD and sugar in the ethanol while stirring and adjusting the pH as necessary to obtain complete dissolution and a clear reaction mixture. The reaction mixture can then be dried to remove the ethanol. No further water washing or filtering is needed.

In this example, an oven-dried single-neck RB flask equipped with a magnetic stir bar was used. Stevioside (200 mg; 0.248 mmol) and Praziquantel (20 mg; 0.064 mmol) were weighed and added into the RB flask followed by adding 2.0 mL absolute ethanol (spectrophotometric grade, 95%). In this example the stevioside to praziquantel is about 9:1. The reaction mixture was vigorously stirred at room temperature for 30 min at 20° C. Ethanol was removed from the mixture via a rotary evaporator under reduced pressure at 35° C. bath temperature resulting in a white solid. The white solid was dried using vacuum drying performed at room temperature and a high vacuum pump for about one hour to remove the ethanol (EtOH) completely using an Edvards Model #RV8 magnetic stirrer, IKA Model C-MAG HS7 rotary evaporator, a Heidolph type Basis Hei-VAP Value, No. 560-00000-0101. The high vacuum pump was connected to a cooling trap and the trap was connected to the RB flask. Vacuum strength was about 1 mm Hg.

Light scattering microscopy of a 1:3 ratio of drug to rubusoside revealed crystal formations not seen for the non-complex form of rubusoside or praziquantel.

The white solid containing the stevioside and praziquantel was then dissolved in 2.0 mL water at room temperature with stirring for 30 min producing a clear solution. The water was removed from the mixture using a rotary evaporator and a high vacuum pump at 35° C. bath temperature resulting in a white foamy solid. The white foamy solid was dried over a high vacuum at room temperature for an additional hour to remove the water completely, by ascertaining changes in weight loss. Drying continued until further weight loss was not observed.

| Solubility of Praziquantel | Without Stevioside | With Stevioside |
|---|---|---|
| In Water | 0.04 g/100 mL | Soluble |
| In Ethanol (95%) | 9.7 g/100 mL | Soluble |
| In Water after first being dissolved w/o in EtOH | Insoluble | Soluble |

EXAMPLE 2—Rebaudioside A and Praziquantel

In this example, like for Example 1 above, the ability of another sugar, rebaudioside A, was assessed for its ability to improve the insolubility of praziquantel. The sugar rebaudioside A (50 mg) and praziquantel (5.0 mg) were mixed in distilled water at a weight ratio of about 9:1. The reaction in distilled water did not solubilize well. The same weight ratio of rebaudioside A and praziquantel were mixed in 95% ethanol (spectrophotometric grade, 95%) in an RB flask at 20° C. As above, the ethanol was removed using a rotary evaporator under reduced pressure at 35° C. bath temperature. The rebaudioside A-praziquantel mixture was hazy and was also observed to re-precipitate after one day at 20° C.

| Solubility of Praziquantel | Without Rebaudioside A | With Rebaudioside A |
|---|---|---|
| In Water | 0.04 g/100 mL | Insoluble |
| In Ethanol (95%) | 9.7 g/100 mL | Insoluble |
| In Water after first being dissolved w/o in EtOH | Insoluble | Insoluble |

EXAMPLE 3—Praziquantel and Sucrose

In this experiment, the method was applied to praziquantel and sucrose. As is shown below, the combination failed to produce a stable complex when assessed by NMR. The combination of praziquantel and sucrose is poorly water-soluble in water and is insoluble in 95% ethanol. The mixture was vigorously stirred at room temperature for 30 min at 20° C. Ethanol was removed via a rotary evaporator under reduced pressure in a 35° C. bath temperature yielding a white solid. The white solid was further dried over a high vacuum for one hour to remove residual ethanol completely, as determined by no further change of weight.

The resulting white solid was then dissolved in deionized water (2.0 mL) at room temperature. The reaction was stirred at room temperature for 30 minutes using a solid magnetic stir bar. Water was then removed using a rotary evaporated under a high vacuum pump at 35° C. bath temperature, which yielded a white foamy solid. The white foamy solid was dried over a high vacuum at room temperature for an additional hour to completely remove the water.

For the experiment, the aqueous solution having sucrose to praziquantel in a 9:1 weight ratio was diluted with ethanol with four parts aqueous solution to one part ethanol (4:1). The addition of ethanol to the aqueous solution improved the solubility. The method and devices for removing the ethanol are described in Example 2. The method failed to create a complex when analyzed by NMR.

EXAMPLE 4—Non-Caloric Sugar Solubility

In this experiment, the following sugars were compared for solubility: rubusoside, dulcoside A, rebaudioside B, dulcoside B, and rebaudioside D. Approximately 5.0 mg of each sugar was attempted to be dissolved in 0.6 mL water and vortexed for 2 minutes at room temperature. No undissolved rubusoside was observed. The dulcoside A and B were partially soluble as well as rebaudioside D. Rebaudioside B was insoluble in water or poorly soluble with no peaks detectable by NMR. It is noted that this is not the hemihydrate crystal, which has a much lower solubility and solution rate than the free form. The solubilities of these sugars in 95% ethanol and water are provided below:

| Sugar | Solubility in Water | Solubility in 95% EtOH |
| --- | --- | --- |
| Rubusoside | Soluble | 10 mg/mL |
| dulcoside A | 2.28 g/L | Partly soluble |
| dulcoside B (also known as rebaudioside C, Reb C) | Partly soluble | Slightly soluble |
| sucrose | 204 g/100 g water | Insoluble |
| D-fructose | ~4000 g/L at 25° C. | Insoluble |
| sucralose | 110 g/L at 20° C. | 283 g/L at 20° C. |
| rebaudioside A (Stevioside A3, Truvia ®) | Poorly soluble | Poorly soluble |
| rebaudioside B (Stevioside A4) | Poorly soluble | Poorly soluble |
| rebaudioside D | 100 mg/ml (88.56 mM) | Insoluble |
| Stevioside (an example of a diterpenoid glycoside) | 4 g/L | 30 mg/ml |
| n-octyl glucose | Soluble | Soluble |
| n-Dodecyl-β-D-maltoside | 50 mg/ml | Soluble |

In another experiment, 50 mg stevia was dissolved in either 2.0 mL water or 2.0 mL 95% ethanol. Stevia was observed to be soluble in both water and ethanol.

In another experiment, 50 mg rebaudioside A was dissolved in either 2.0 mL water or 2.0 mL 95% ethanol. Rebaudioside A was observed to be soluble in water and either insoluble or partially soluble in ethanol.

In another experiment, 50 mg sucralose was dissolved in either 2.0 mL water or 2.0 mL 95% ethanol. Sucralose was observed to be soluble in water and slowly soluble in ethanol. By slowly soluble in this experiment, the sucralose took 2 hours at room temperature to dissolve.

In another experiment, 50 mg n-dodecyl-β-D-maltoside was dissolved in either 2.0 mL water or 2.0 mL 95% ethanol. N-dodecyl-β-D-maltoside was observed to be soluble in water and ethanol.

In another experiment, 50 mg n-octyl glucose was dissolved in either 2.0 mL water or 2.0 mL 95% ethanol. The n-octyl glucose was observed to be soluble in water and ethanol.

EXAMPLE 5—Rubusoside and Sildenafil

In a prophetic example, a 9:1 ratio of rubusoside (50 mg) to sildenafil (5 mg) (VIAGRA®) is mixed in 2.0 mL 95% ethanol to produce a mixture and allowed to dissolve at 20° C. The ethanol of the mixture is then evaporated. The resulting powder is then resolubilized in 2.0 mL water and the NMR of the solid is assessed to determine whether a complex has formed. NMR indicated that a complex had formed. In all the examples with sildenafil, the sildenafil used was obtained from Ambeed Chemicals, Cas #57817-89-7. Possible hydrogen bonds that can be formed to create the complex are depicted in FIG. 1. It should be noted that sildenafil may be categorized as being moderately water-soluble. However, improving water-solubility of a moderately soluble drug, will benefit how much drug must be administered to a subject, as well as if it is to be used to cross a skin barrier in the form of a topical application. Thus improving the water-solubility of a moderately water-soluble ED drug is also contemplated herein.

EXAMPLE 6—Sildenafil and Stevioside

A 1:2 mole ratio of sildenafil (5 mg) to stevioside (84.8 mg) was dissolved in 50 mL 85% ethanol in an RB flask with stirring by a magnetic stir bar. The pH of the reaction mixture was adjusted to 5.8 with 0.1 N citric acid at 20° C. Once dissolved, the ethanol was removed by drying with a rotary evaporator to obtain a white crystal powder.

The powder comprising the complex form of sildenafil and stevia was placed in gastric juice having a pH of 8.5 at 20° C. and observed for 4 hours (Carolina Gastric juice, artificial laboratory grade obtained at www.carolina.com/specialty-chemicals-d-1/gastric-juice-artificial-laboratory-grade-500-ml/864603.pr, comprises water 99.18, pepsin 0.5% Cas #9001-75-6, HCl 0.22% Cas #7647-01-0, thymol 0.1%, 89-83-8). No precipitate was observed even after 4 hours at a pH of 8.5 at 20° C.

Stability at this pH is relevant as this is the pH of the duodenum. An orally administered pill (e.g., tablet, chewable gummy, capsule and the like) absent any coating will reside for about 2-4 hours in the stomach before passing to the small intestine and then to the large intestine. No precipitate was observed and the solution remained colorless. The pH of the liquid sample of sildenafil-stevioside was about a pH of 4.8 before adding it to the gastric juice. The gastric juice was assessed and raised back to a pH of 8.5 after the addition of the liquid sample of sildenafil-stevioside complex.

EXAMPLE 7—Stevioside and Sildenafil

In another test, it was observed that a 2:1 molar ratio of stevioside:sildenafil produced a complex when prepared using the same method as in Example 6. The method of Example 6 was used to assess the stability of the 2:1 molar ratio of sugar to drug in the complex under conditions emulating the duodenum. 1.2 mg of the formed complex was placed in a gastric juice environment of 1.5 mL and the pH was lowered to 2.0. The complex remained stable for at least 4 hours.

EXAMPLE 8—Stevioside and Sildenafil

Step 1: In an oven-dried single neck RB flask equipped with magnetic stir and septa (flask cap), 5 mg sildenafil (0.01054 mmol) and 16.95 mg stevioside (1:2 molar ratio) were weighed into the RB flask and dissolved in 85% ethanol (~2.0 mL, denatured 85% ethanol) at ambient temperature. The reaction mixture was vigorously stirred at room temperature for 30 min. The resulting solution was either slightly hazy or had visible solid particles present. 0.1 N citric acid was added to the solution making the solution homogeneous and clear; the addition of the citric acid reduced the pH from 6.1 to 5.5. Then the ethanol was removed via a rotary evaporator under reduced pressure at 35° C. bath temperature thereby obtaining a white solid. The white solid was dried over a high vacuum for an hour to remove the ethanol completely (no further reduction in weight was observed).

Step 2: The obtained white solid was then dissolved in 2.0 mL water at room temperature in an RB flask with a magnetic stir bar. The reaction mixture was stirred at ambient temperature for 30 min. Water was removed using a rotary evaporator and a high vacuum pump in a 35° C. bath temperature thereby obtaining a white foamy solid. The white foamy solid was dried over a high vacuum at room temperature for an additional hour to remove the water completely. The weight of the flask was checked while drying until no further weight loss was observed. NMR showed that peaks present that indicated 100% solubility of the sildenafil in water.

In another experiment using a 1:10 molar ratio of Sildenafil:Stevioside (5 mg: 84.8 mg) was solubilized using the same steps as above for Step 1. Both compounds were slowly soluble; after 30 minutes, the compounds appeared to have dissolved but the solution appeared slightly hazy. The ethanol was then dried to obtain a solid.

The Sildenafil:Stevioside solid was then dissolved in 2 mL water as described in Step 2 above and appeared to solubilize immediately. However, after a couple of minutes, a white turbid precipitate started forming. The white turbid solution became whiter after 30 min. After concentration, 89.8 mg of the solid was dissolved in 2.0 mL D20 and analyzed by NMR. The solution again appeared white and turbid and did not rapidly solubilize. The NMR indicated that sildenafil did not form a complex with stevioside when using the 1:10 ratio.

EXAMPLE 9—1:10 Molar Ratio of Sildenafil and Stevioside

The 1.0:10.0 molar ratio of Sildenafil:Stevioside (5 mg: 84.8 mg) obtained by the method described in Example 8 at the end of Step 2 was then dissolved in 2.0 ml distilled water. The reaction mixture was determined to have a pH of 6.4 and appeared white and turbid. To the turbid white solution was added 50 µL 0.1 N HCl, and the solution became less turbid and had a pH of about 5.8. When another 50 µL 0.1 N HCl (total of 100 µL) was added to the solution, the pH became about 5.2 and turbidity additionally decreased but remained. When another 50 µL 0.1 N HCl (i.e., a total of 150 µL) was added to the solution, the solution became clear and homogeneous and had a pH of about 4.8. The clear solution was then dried as described in Step 2 in Example 8. The 10 mg dried solid was then dissolved in 0.6 mL D20. NMR revealed that the 1:10 ratio of sildenafil to stevioside with the addition of the acid produced a drug-sugar complex, and the complex was determined to be 100% soluble in water using this method. Additionally, when the sample in D20 was held at room temperature for 3 days, no precipitate was observed to form.

EXAMPLE 10—Sildenafil and Stevioside

In another experiment, a 1:10 weight ratio of sildenafil and stevioside was assessed for whether a complex could form when using an electrolysis machine instead of an acid. Sildenafil (5 mg; 0.01054 mmol) and stevioside (50 mg, 0.0778 mmol) were treated as follows.

Step 1: In a fresh 20 mL clear RB flask, 5 mg sildenafil and 50 mg stevioside were dissolved in 2.0 mL of 85% ethanol at ambient temperature. The reaction mixture was stirred for 15 min and produced a hazy solution.

An electrolysis machine was set up using electrodes (anode and cathode) that were dipped into the reaction mixture with platinum and copper metal plates. The reaction mixture was vigorously stirred at room temperature for 30 min while sending low to high electric energy, i.e., the voltage applied started at 3vDC to 24 vDC over 30 min. The reaction mixture remained hazy or had visible solid particles present. The ethanol was removed from the reaction mixture using a rotary evaporator under reduced pressure at 35° C. bath temperature to get a white solid as described above. The white solid was dried over a high vacuum for an hour to remove the ethanol completely and was confirmed by the absence of further weight loss.

Step 2: A magnetic stir bar was added into the flask having the dried white solid and 2.0 mL distilled water was added to dissolve the solid at room temperature. The reaction mixture was stirred at ambient temperature for 20 min. The solution became white and turbid. The above electrolysis method was applied for 30 min, and the solution was observed to turn a light yellow-orange color due to metals. The water was removed using the rotary evaporator under a high vacuum pump at 35° C. bath temperature thereby obtaining a white foamy solid. The white foamy solid was further dried over a high vacuum at room temperature for an additional hour to remove the water completely. The weight of the sample was analyzed while drying until no further weight loss was observed thus indicating that all water had been removed.

A 7 mg sample was then dissolved in 6.0 mL D20 for NMR analysis. NMR indicated that the sildenafil did not form a complex with stevioside under these conditions.

EXAMPLE 11—1:5 Molar Ratio of Sildenafil to Stevioside

In this example, a 1:5 molar ratio of sildenafil to stevioside was examined with the addition of hydrochloric acid (HCl) to ascertain whether a water-soluble complex could be formed at this ratio using an acid. Step 1: 5 mg of sildenafil and 42.41 mg of stevioside were dissolved in 2.0 mL 95% ethanol. The compounds were again observed to slowly dissolve forming a lightly hazy solution after 3 minutes; the resulting solution had a pH~5.2.

To the hazy solution was added 50 µL 0.1 N HCl, causing the solution to become clear and homogeneous; the acid-containing solution had a pH of ~4.9. The reaction mixture was then dried as described in Example 8 to produce a solid.

The dried solid was then dissolved in 2.0 mL distilled water; it was noticed that the solid dissolved immediately and produced a clear homogeneous solution. When an additional 50 µL 0.1 N HCl was added to the solution, no change was discerned in the reaction mixture.

For NMR, 10 mg of the solid sample obtained was dissolved in 0.6 mL D20. The dissolved 10 mg sample again produced a clear and homogeneous solution. 1H-NMR displayed drug peaks in an equimolar ratio (1:5), indicating 100% solubility of the sildenafil-stevioside complex in water and that a complex between the drug and sugar had formed. The complex in D20 remained stable for 9 days without any observable precipitate forming.

EXAMPLE 12—Complex of Sildenafil, Rubusoside and Stevioside

In this example, sildenafil was combined with two sugars, rubusoside, and stevioside, and then analyzed. The following ratio of Sildenafil:Rubusoside:Stevioside was used: 1.0: 7.38:1.0 molar ratio; 5 mg: 50.0 mg: 8.4 mg.

Step 1: The three materials were weighed and placed in an RB flask and dissolved in 2.0 mL of 95% ethanol. The reagents were observed to slowly dissolve and produced a reaction mixture with a pH of ~6.1. The reaction mixture was dried as previously described.

Step 2: The dried reaction mixture was then dissolved in 2.0 ml distilled water (pH~6.1) wherein the solid was observed to dissolve immediately. However, a precipitate was observed to form after allowing the solution to sit for 30 minutes. To the precipitated reaction mixture, 1 drop of 1 N HCl was added, whereupon the reaction mixture became clear and homogeneous. It should be noted, that in some instances the acid, base, or buffer can be added during step 1 or in step 2. The pH of the resulting reaction mixture was ~2.0. The reaction mixture was then dried as described in Example 7.

The dried solid obtained after the addition of the drop of HCl was analyzed by NMR, wherein 10 mg of the dried sample was dissolved in 0.6 mL D20, producing a clear homogeneous solution. The 1H-NMR analysis demonstrated that drug peaks were present in an equimolar ratio of sildenafil to rubusoside to stevioside, indicating 100% solubility of the sildenafil-stevioside complex in water. The solution dissolved in D20 remained clear and homogeneous without forming a precipitate for 3 days.

The relevance of this example is that different steviol sugars can be combined to form the complex, as long as an acid is used to solubilize the reagents.

EXAMPLE 13—1:5 Molar Ratio of Sildenafil to Stevioside with Citric Acid

In this experiment, citric acid was analyzed for its ability to improve the formation of a sildenafil-stevioside complex at a 1:5 molar ratio of sildenafil to stevioside. 5 mg of sildenafil and 42.41 mg stevioside were dissolved in 95% ethanol at ambient temperature with stirring as described above. The reaction mixture slowly solubilized after 3 minutes producing a slightly hazy solution at a pH of 5.2. When 50 µL of 0.1 N citric acid was added to the solution, the solution became clear and homogeneous and had a pH of 5.8. The reaction mixture was dried as described in Example 7. The dried solid was dissolved in 2.0 mL of distilled water and was observed to immediately dissolve and produce a clear homogeneous mixture.

The dissolved mixture was dried again as described in Example 7. 10 mg of the dried solid sample was dissolved in 0.6 mL D20, producing a clear homogeneous reaction mixture. When analyzed by 1H-NMR, drug peaks were observed that indicated a complex was formed and indicative of 100% solubility of the complex in water demonstrating that citric acid can also assist in complex formation. The reaction mixture was stable for 3 days without the formation of a visible precipitate.

EXAMPLE 14—1:3 Molar Ratio of Sildenafil to Stevioside Molar Ratio with Citric Acid In this experiment, a 1:3 molar ratio of sildenafil and stevioside was made and adjusted using citric acid to see if complete solubilization could be obtained. 5.0 mg sildenafil and 25.44 mg stevioside were dissolved in 2.0 mL 95% ethanol producing a solution that appeared slightly hazy and had a pH of ~5.2. When 50 µL 0.1 N citric acid was added to the reaction mixture, the solution became clear and homogeneous and had a pH of ~4.9. The reaction mixture was then dried as described above.

The dried solid obtained from the citric acid-treated reaction mixture was then dissolved in water producing a reaction mixture having a pH of 5.5. The solid was observed to immediately dissolve in the distilled water and produced a clear homogeneous solution. To this solution, 50 µL of 0.1 N citric acid was added. The solution with the added citric acid remained clear and had a pH of ~4.6. The reaction mixture having a pH of 4.6 was dried as previously described until all water was removed.

10 mg of the dried reaction mixture was dissolved in 0.6 mL D20 producing a solution that was homogeneous and clear. 1H-NMR yielded drug peaks that were present in an equimolar ratio of 1:3, indicating 100% solubility of sildenafil in water in the complex. The D20 solubilized 1:3 molar ratio complex remained in solution for 3 days.

EXAMPLE 15—1:2 Molar Ratio of Sildenafil to Stevioside with Citric Acid

In this experiment, a 1:2 molar ratio of sildenafil to stevioside was analyzed for solubilization with the aid of citric acid for solubilization. For the experiment, 5.0 mg sildenafil and 16.95 mg stevioside were dissolved in 50 ml distilled water. The resulting reaction mixture was solubilized after 3 minutes of stirring but remained hazy and had a pH of 6.1. To this reaction mixture, 100 µL 0.1 N citric acid was added and the resulting reaction mixture became clear and homogeneous (i.e., no longer hazy). The homogeneous mixture had a pH of 5.5. The mixture was dried as described above to obtain a white solid.

When the reaction mixture was dissolved again in 2.0 mL distilled water, the solid immediately dissolved producing a homogeneous and clear solution. The solid was then dried again as described above.

10.0 mg of the obtained white solid was dissolved in 0.6 mL D20, immediately becoming a clear solution. The solution was analyzed by 1H-NMR confirming the presence of a sildenafil-stevioside complex having a 1:2 equimolar ratio and indicating 100% solubility of the sildenafil complex in water.

EXAMPLE 16—1:2 Molar Ratio of Praziquantel to Rubusoside with HCl

In this example, a 1:2 molar ratio of praziquantel to rubusoside was analyzed with the addition of HCl. For example, 5 mg of praziquantel and 20.57 mg of stevioside were admixed in 2.0 mL of 95% ethanol. Dissolution of the compounds proceeded slowly with both compounds appearing to be dissolved after 3 minutes. The resulting solution had a pH of ~5.2 and appeared slightly hazy. 25 µL of 0.1 N HCl was added to the solution, whereupon the haziness completely disappeared. The reaction mixture was then dried as described above to produce a white solid.

The obtained white solid was then solubilized with 2.0 mL distilled water producing a mixture having a pH of ~4.7. The dissolution was immediate and produced a clear solution; however, after 15 minutes, the solution became white and turbid.

When 10 mg of the white solid obtained above was dissolved in 0.6 mL D20, a white turbid solution again was produced. NMR of the solution indicated only partial solubility of the praziquantel in water at the 1:2 molar ratio. Therefore, the molar ratio of the rubusoside and the insoluble drug praziquantel, as shown in this example, is also relevant to solubility. Solubilization of a drug is not linear as indicated by these results.

EXAMPLE 17—Assessment of Treatment Against S. mansoni In Vitro

This experiment is provided to show that a water-soluble complex comprising praziquantel and rubusoside remained effective in killing blood trematodes, as evidence that the complex is soluble and maintains parasite-killing activity.

Schistosoma mansoni is a water-borne parasite that impacts humans. It is a member of the blood fluke (i.e., blood trematode) family. Other types of blood trematodes causing Schistosomiasis include S. mekongi, S. intercalatum, S. japonicum, and S. guineensis (previously considered synonymous with S. intercalatum). These organisms can also parasitize birds and mammals. When a human is infected, the adult form of the parasite resides in the blood vessels near the human intestine causing intestinal schistosomiasis, wherein the clinical symptoms are caused by the laying of eggs.

In this experiment, approximately 130 *S. mansoni* newly transformed schistosomula (NTS) skin-stage schistosome worms 1 day after transformation from infective cercariae were cultured overnight in M199 medium at 37° C. in a 5% $CO_2$ incubator. Following overnight incubation, the NTS were exposed to different concentrations of either praziquantel alone or praziquantel complexed with rubusoside for 24 and 72 hours. Worm images were taken using a Keyence BZ-X800 microscope and rubusoside and praziquantel activity was evaluated phenotypically. Both the uncomplexed form of praziquantel and the praziquantel-rubusoside complex had similar activity in killing parasites. The following table indicates the number of worms remaining alive after dosing with either the sugar-free praziquantel or the rubusoside-praziquantel complex.

| Compound | 24 hr Exposure $LD_{50}$ (μM) | 72 hr exposure $LD_{50}$ (μM) |
|---|---|---|
| Rubusoside-Praziquantel complex | 25.9 ± 0.91 | 15.9 ± 0.25 |
| Praziquantel alone | 33.5 ± 5.71 | 24.3 ± 0.67 |

NTS viability was assessed by scoring worms based on outlined criteria as indicated below. NTS viability was also assessed by measuring the ATP content of the worms using Promega's CellTiter-Glo® Luminescent Cell Viability Assay according to the manufacturer's instructions. The experiment was performed in triplicate. The effect of the rubusoside and praziquantel (PZQ) was determined using the formula of % Effect=100−(Average (Test)×100/Average (Control)). From this, the $LD_{50}$ was then calculated.

Exposure after 72 hours demonstrated that the praziquantel-only had an $LD_{50}$ on the organism of 33.9±0.64 μM. The formulation of rubusoside-praziquantel produced an $LD_{50}$ of 18.3±0.94 μM. The difference in impact on the viability of the worms between praziquantel alone and in the praziquantel-rubusoside form was not scientifically statistically significant. Scoring Criteria:
- 3=motile, no changes to morphology or transparency of the fluke worm
- 2=reduced motility and/or some damage to the tegument is noted as well as reduced transparency and granularity
- 1=severe reduction of motility and/or damage to the tegument observed with high opacity and high granularity
- 0=dead EXAMPLE 18—Dulcoside A and Praziquantel In this experiment, a weight ratio of 84:16 (or 5.25:1) of Dulcoside A (28 mg) to Praziquantel (4.5 mg) was used. Both dulcoside A and praziquantel are insoluble in 95% ethanol and a water bath at 20° C. Dulcoside A was determined to be unable to form hydrogen bonds with praziquantel using the described method to increase the solubility of praziquantel. This example demonstrates that not all stevia sugars can solubilize a drug in 95% ethanol, while another of the indicated sugars can.

EXAMPLE 19—Rebaudioside B and Praziquantel

In this experiment, a weight ratio of 9:1 of rebaudioside B (28 mg) to Praziquantel (3 mg) was used. Both rebaudioside B and praziquantel are insoluble in 95% ethanol and a water bath at 20° C. Rebaudioside B was determined to be unable to form hydrogen bonds to praziquantel using the described method to increase the solubility of praziquantel. This example demonstrates that not all stevia sugars can solubilize a drug, while other stevia sugars can.

EXAMPLE 20—Dulcoside B and Praziquantel

In this experiment, a weight ratio of 9:1 of dulcoside B (50 mg) to Praziquantel (5.0 mg) was used in 2.0 mL 95% ethanol at 20° C. Like in the rubusoside-praziquantel experiment, it was observed that the materials were slowly dissolving in the ethanol. After about 10 minutes, the reaction mixture became a clear and colorless solution. The ethanol was removed as described in the other examples and 2.0 mL of water was added to the sample. Again, the powder re-dissolved in water becoming a clear and colorless solution. NMR confirmed that a complex was formed between dulcoside B and praziquantel and that the complex is well soluble in water when in a complex.

EXAMPLE 21—Rebaudioside D and Praziquantel

In Step 1, a weight ratio of 9:1 of rebaudioside D (50 mg) to Praziquantel (5.0 mg) was used. Both rebaudioside D and praziquantel are insoluble in 95% ethanol and in water at 20° C. Rebaudioside D was determined to be unable to form hydrogen bonds (and thus a complex) with praziquantel using the described method. The insolubility of the combination and the lack of complex formation were determined by NMR. This example demonstrates that not all stevia sugars can solubilize a drug, while another listed sugar can.

EXAMPLE 22—D-Glucose or D-Fructose and Praziquantel

In this experiment, D-glucose was mixed with praziquantel at a 9:1 weight ratio. 200 mg of D-glucose and 20 mg of praziquantel were insoluble in both 95% ethanol and water at 20° C. D-glucose is soluble in water, but the praziquantel was observed to stick to the walls of the flask. From this experiment, it was determined praziquantel could not be made more soluble using D-glucose and did not form a complex with D-glucose, as confirmed by NMR.

The same experiment was performed with D-fructose instead of D-glucose. In this experiment, 200 mg of D-fructose and 20 mg praziquantel for a 9:1 weight ratio at 20° C. were stirred in the presence of 95% ethanol. The D-fructose is not soluble in 95% ethanol but is soluble in water. NMR determined that D-fructose and praziquantel did not form a complex and did not make praziquantel soluble or more soluble in water.

EXAMPLE 23—Rubusoside and Prednisone

In this example, 50 mg of rubusoside and 5 mg of prednisone were mixed in 2.0 mL 95% ethanol at 20° C., which also is a 9:1 weight ratio of the sugar (rubusoside) to the drug (prednisone) with stirring as discussed above. The reaction mixture was slow to solubilize. After 5 minutes at 20° C., the reaction mixture became a clear colorless solution. The ethanol was removed from the mixture using a rotary evaporator and a high vacuum pump at 35° C. bath temperature. The dried powder was then re-dissolved in 2 mL of deionized water producing a homogeneous, white turbid mixture having a syrup consistency.

NMR was used and determined that the method did not produce a rubusoside-prednisone complex that was water-soluble. NMR only revealed trace NMR peaks.

In another example, testosterone cypionate was tested with rubusoside at a 3:1 sugar-to-drug ratio using 23.4 mg rubusoside and 5 mg testosterone cypionate. Both were slowly soluble in 85% (denatured) ethanol becoming a clear and colorless solution. However, after the mixture was dried and then dissolved in water, only a white turbid solution formed. NMR indicated that no complex had formed. Testosterone cypionate was also tested in a 1:10 molar ratio with a sugar. The Testosterone cypionate and stevioside dissolved in 85% ethanol as before. However, after drying, the powder again produced a white-turbid solution when solubilized in 2 mL water. Citric acid (0.1 N) was added to the solution but no change in the white turbid solution was seen. NMR showed that the addition of the citric acid failed to form a complex. weight ratio, but it also failed to form a complex with rubusoside (data not shown). The same ratio was also tested using a 0.2 M sodium carbonate and carbonate buffer at pH 9.4. The use of a basic buffer also failed to form a complex when assessed by NMR. The same 1:10 molar ratio experiment was also performed with 0.1 N aqueous sodium hydroxide being used to see if the white turbid solution would change. NMR again showed that no complex was formed.

EXAMPLE 24—Penicillin V and Rubusoside

Rubusoside (50 mg) and penicillin V (phenoxymethylpenicillinic acid) (5.0 mg) at a weight ratio of 9:1 were dissolved in 95% ethanol (2.0 mL) at 20° C. The ethanol was removed from the mixture via a rotary evaporator under reduced pressure at 35° C. bath temperature resulting in a powder. The solid was then dissolved in water demonstrating that a complex had been formed between rubusoside and penicillin V.

| Solubility of Penicillin V HCl (350.4 MW) | Without Rubusoside | With Rubusoside |
| --- | --- | --- |
| In Water | 0.636 mg/mL or at pH 1.8 acidified with HCl at 24 mg/100 mL | Soluble |
| In Ethanol | Soluble | Soluble |
| In Water after first being dissolved w/o in EtOH | N/A | Soluble |

EXAMPLE 25—Acyclovir and Rubusoside

Acyclovir has a solubility of less than 1 mg/ml which generally means that it is considered slightly soluble or insoluble. In this experiment, rubusoside (50 mg) and acyclovir (5 mg) at a weight ratio of 9:1 were dissolved in 2.0 mL 95% ethanol at 20° C. The ethanol was removed from the mixture via a rotary evaporator under reduced pressure at 35° C. bath temperature resulting in a powder. The solid was then dissolved in water demonstrating that a complex had been formed between rubusoside and acyclovir.

| Solubility of Penicillin V HCl (350.4 MW) | Without Rubusoside | With Rubusoside |
| --- | --- | --- |
| In Water | 24 mg/100 mL at pH 1.8 Or less than 1 mg/mL at 55° C. | Soluble |
| In 95% Ethanol | Soluble | Soluble |
| In Water after first being dissolved w/o in EtOH | N/A | Soluble |

EXAMPLE 26—Rubusoside and Ibuprofen

In a prophetic example, a 9:1 weight ratio of rubusoside (50 mg) to ibuprofen (5.0 mg) is mixed (stirred) in 2.0 mL 95% ethanol to produce a mixture and allowed to dissolve at 20° C. The ethanol of the mixture is then evaporated. The resulting powder is then resolubilized in 2.0 mL water and the NMR of the solid was assessed for the presence of new hydrogen bonds linking the ibuprofen to rubusoside.

EXAMPLE 27—Rubusoside and Aceclofenac

In a prophetic example, a 9:1 weight ratio of rubusoside (50 mg) to aceclofenac (5.0 mg) is mixed in 2.0 mL 95% ethanol and allowed to dissolve at 20° C. to produce a mixture; the ethanol is then removed as described. The resulting powder is then resolubilized in 2.0 mL water and the NMR of the solid is assessed for the presence of new hydrogen bonds linking rubusoside to aceclofenac.

Aceclofenac is a non-steroidal anti-inflammatory drug. Diclofenac is its analog. It would be reasonable to expect that diclofenac would also be solubilized in the same manner as aceclofenac. Diclofenac is a metabolite of aceclofenac, as are 4'-hydroxyaceclofenac (the major metabolite), 5-hydroxyaceclofenac, 4'-OH-aceclofenac, and 5-OH-aceclofenac. Aceclofenac salts include salts with cytosine, piperazine, L-lysine, and gamma-aminobutyric acid and are also contemplated for solubilization using the methods disclosed herein.

EXPERIMENT 28—Rubusoside and Paclitaxel

Rubusoside and paclitaxel at a weight ratio of 9:1 (50 mg to 5 mg) slowly dissolved in 95% ethanol that after 10 minutes at 20° C. yielded a homogeneous clear colorless solution. When the same amount of paclitaxel was dissolved in the same volume of water, a white turbid liquid was produced, which remained even after 30 minutes. It was determined that the method cannot produce a hydrogen-bonded complex that is soluble in water.

Ethanol was removed from the mixture via a rotary evaporator under reduced pressure at 35° C. bath temperature resulting in a white-colored solid. The dried solid was then dissolved in water. The solution was observed to be white and turbid after 30 minutes with no colorless or clear solution being obtained indicating that complexation between rubusoside and paclitaxel had occurred.

| Solubility of Paclitaxel | Without Rubusoside | With Rubusoside |
| --- | --- | --- |
| In Water | 0.1 µg/ml | Insoluble |
| In Ethanol | 1.5 mg/ml | Soluble |
| In Water after first being dissolved w/o in EtOH | N/A | Insoluble |

The white solid containing the rubusoside and paclitaxel was then dissolved in 2.0 mL water at room temperature with stirring for 30 min producing a clear solution. The water was removed from the mixture using a rotary evaporator and a high vacuum pump at 35° C. bath temperature resulting in a white foamy solid. The white foamy solid was dried over a high vacuum at room temperature for an additional hour to remove the water completely, by ascertaining changes in weight loss. Drying continued until further weight loss was not observed.

More than ten intermolecular hydrogen bonds are possible between rubusoside and paclitaxel (e.g., OH—O; OH—N; and NH—O). Paclitaxel has a molecular weight (MW) of 853.92 and an elemental analysis of C, 66.11; H, 6.02; N, 1.64; and O, 26.23.

EXAMPLE 29—Praziquantel and Sucrose

In this experiment, the method was applied to praziquantel and sucrose. The combination of praziquantel and sucrose is poorly soluble in water and is insoluble in 95% ethanol. The mixture was vigorously stirred at room temperature for 30 min at 20° C. Ethanol was removed via a rotary evaporator under reduced pressure in a 35° C. bath temperature yielding a white solid. The white solid was further dried over a high vacuum for one hour to remove residual ethanol completely, as determined by no further change of weight.

The resulting white solid was then dissolved in deionized water (2.0 mL) at room temperature. The reaction was stirred at room temperature for 30 minutes using a solid magnetic stir bar. Water was then removed using a rotary evaporated under a high vacuum pump at 35° C. bath temperature, which yielded a white foamy solid. The white foamy solid was dried over a high vacuum at room temperature for an additional hour to completely remove the water.

For the experiment, the aqueous solution having sucrose to praziquantel in a 9:1 weight ratio was diluted with ethanol with 4 parts aqueous solution to 1 part ethanol (4:1). The addition of ethanol to the aqueous solution improved the solubility. The method and devices for removing the ethanol are described in Example 2. The experiment failed to produce a complex between the praziquantel and sucrose.

| Solubility of Praziquantel | Without Sucrose | With Sucrose |
|---|---|---|
| In Water | 0.04 g/100 mL | Insoluble |
| In Ethanol (95%) | 9.7 g/100 mL | Insoluble |
| In Water after first being dissolved w/o in EtOH | Insoluble | Insoluble |

EXAMPLE 30—Increasing Rubusoside to Praziquantel Ratios

In this experiment, the optimum molar ratio of rubusoside and praziquantel were assessed.

Step 1: In an oven-dried single-neck RB flask equipped with a magnetic stir bar and septa (for sealing the flask) was placed a 2:1 ratio of rubusoside (10.0 mg; 15.56 mmol) and praziquantel (5.0 mg; 16.00 mmol). Ethanol (1 mL) was added to the RB flask. The reaction mixture was vigorously stirred at room temperature for 30 min. This produced a clear solution. Ethanol was removed via a rotary evaporator under reduced pressure at 35° C. bath temperature to get a white solid. The white solid then was dried using a high vacuum for an hour to remove residual ethanol completely.

Step 2: The white solid obtained from Step 1 was then dissolved in 1.0 mL deionized water using a magnetic stir bar in the RB flask at room temperature. The reaction mixture was stirred at ambient (room temperature) for 30 min. A hazy solution with some particles was observed. The water was removed using a rotary evaporator using a high vacuum pump wherein the RB flask was in a 35° C. bath temperature and when dried produced a white foamy solid. The white foamy solid was dried over a high vacuum at room temperature for an additional hour to remove the water completely. The weight was checked while drying until further weight loss was not found. The rubusoside to praziquantel mole ratio from this experiment is 0.01556 to 0.016 which is 0.972:1.00 (nearly 1:1). Both materials were observed to be soluble in ethanol to produce a clear colorless solution. When the materials were solubilized in water, the solids were observed to slowly dissolve with the final solution being hazy and still having particles present. 1H-NMR analysis showed an increase in solubility for the drug of 1.5 to 1.73 also indicating the formation of a complex.

| Material | Molecular Weight | Weight | Milli moles (mmol) | Equivalents |
|---|---|---|---|---|
| Rubusoside | 642.74 | 10 mg | 0.01556 | 0.972 |
| Praziquantel | 312.41 | 5 mg | 0.016 | 1.00 |

The same experiment was performed at a 1:1 ratio of rubusoside to praziquantel. In an oven-dried single-neck RB flask equipped with a magnetic stir bar and septa, a 1:1 ratio of rubusoside (10.0 mg) and praziquantel (10.0 mg) was placed. Ethanol (95%) (1 mL) was added to the RB flask. The reaction mixture was vigorously stirred at room temperature for 30 min. Ethanol was removed via a rotary evaporator under reduced pressure in a 35° C. water bath. A white solid was obtained and then further dried over a high vacuum for an hour to remove residual ethanol completely. To the obtained white solid was added a magnetic stir bar and the solid was solubilized in de-ionized water (1.0 mL) at room temperature. The reaction mixture was stirred at ambient temperature for 30 min. The reaction mixture was not soluble and became a white solid. Stirring continued for another 2 hours, but no change in solubility was observed for the 1:1 ratio of compounds. Water was removed using a rotary evaporator and a high vacuum pump with the RB flask again in a 35° C. water bath to yield a white foamy solid. The white foamy solid was dried over a high vacuum at room temperature for an additional hour to remove the water completely. The weight was checked while drying and the white compound dried until further weight loss was not found. The rubusoside to praziquantel mole ratio is 0.01556: 0.032 which is 0.45:1.00 (approximately 1:2) as seen in the table below. Both materials were soluble in ethanol and less soluble in water.

| Material | Molecular Weight | Weight | Milli moles (mmol) | Equivalents |
|---|---|---|---|---|
| Rubusoside | 642.74 | 10 mg | 0.01556 | 0.45 |
| Praziquantel | 312.41 | 10 mg | 0.032 | 1.00 |

The 1H-NMR analysis determined that the 1:1 ratio for rubusoside and praziquantel did not work to form a complex between rubusoside and praziquantel. Solubility was found to decrease from 1.5 to 0.89.

The same experiment was performed using a 3:1 ratio of rubusoside to praziquantel. While solubility did increase, this ratio was determined to be not as soluble as the 2:1 ratio of rubusoside to praziquantel. Using the same procedure described for the 1:1 and 2:1 ratio examples, 7.5 mg of rubusoside and 2.5 mg of praziquantel were dissolved in 1 ml of 95% ethanol to produce a clear colorless solution. When the same ratio was dissolved in deionized water after the ethanol dissolving step, initially a solid was present, but it slowly dissolved producing a slightly hazy solution with no discernable particles. Analysis by 1H-NMR determined that the 3:1 ratio rendered the praziquantel less soluble, decreasing from 1.5 to 0.65. The rubusoside to praziquantel mole ratio is 0.07001 to 0.04801, which is 1.48:1 or approximately a 3:2 ratio. The 1:1 ratio worked but not as well.

| Material | Molecular Weight | Weight | Milli moles | Equivalents |
| --- | --- | --- | --- | --- |
| Rubusoside | 642.74 | 45 mg | 0.07001 | 1.46 |
| Praziquantel | 312.41 | 15 mg | 0.04801 | 1.00 |

In another example, rubusoside and praziquantel were analyzed at a 4:1 weight-to-weight (50 mg and 12.5 mg respectively). The compounds were dissolved and treated as described above for the other examples. The ethanol-dissolved compounds produced a clear solution, while the water-dissolved particles produced a hazy solution but no particles were visually discernable. The rubusoside to praziquantel mole ratio is 0.07780 to 0.04001, which is 1.94:1 or approximately 2:1.

| Material | Molecular Weight | Weight | Milli moles | Equivalents |
| --- | --- | --- | --- | --- |
| Rubusoside | 642.74 | 50 mg | 0.0778 | 1.94 |
| Praziquantel | 312.41 | 12.50 mg | 0.04001 | 1.00 |

Rubusoside and praziquantel were then assessed at a 5:1 ratio (50 mg:10 mg) following the same procedures. In ethanol, both materials dissolved easily producing a clear and colorless solution. When the compounds were dissolved in water, the solids slowly dissolved producing a slightly hazy solution with visible particles. The rubusoside to praziquantel mole ratio is 0.0778 to 0.03201, which is 2.43:1.

| Material | Molecular Weight | Weight | Milli moles | Equivalents |
| --- | --- | --- | --- | --- |
| Rubusoside | 642.74 | 50 mg | 0.0778 | 2.43 |
| Praziquantel | 312.41 | 10 mg | 0.03201 | 1.00 |

Rubusoside and praziquantel were then assessed at a 6:1 weight/weight ratio (60 mg to 10 mg) using the same methods as described above. Both compounds were soluble in ethanol producing a clear and colorless solution. When the compounds are dissolved in water, initially there was a solid, which solely dissolved over time producing a slightly hazy solution with no particles present. The rubusoside to praziquantel mole ratio is 0.09335 to 0.03201, which is 2.92:1.

| Material | Molecular Weight | Weight | Milli moles | Equivalents |
| --- | --- | --- | --- | --- |
| Rubusoside | 642.74 | 60 mg | 0.09335 | 2.92 |
| Praziquantel | 312.41 | 10 mg | 0.03201 | 1.00 |

Rubusoside and praziquantel were then assessed at a 7:1 weight/weight ratio (70 mg to 10 mg respectively) using the same methods as described above. Both compounds were soluble in ethanol producing a clear and colorless solution. When the compounds are dissolved in water, the compounds were readily soluble with no particles observed.

| Material | Molecular Weight | Weight | Milli moles | Equivalents |
| --- | --- | --- | --- | --- |
| Rubusoside | 642.74 | 70 mg | 0.109 | 3.40 |
| Praziquantel | 312.41 | 10 mg | 0.03201 | 1.00 |

The rubusoside to praziquantel mole ratio is 0.109 to 0.03201, which is 3.40:1. Therefore, solubility may work equally as well as a 3:1 mole ratio for rubusoside to praziquantel.

Rubusoside and praziquantel were then assessed at a 9:1 weight/weight (w/w) ratio (50 mg to 5 mg respectively) using the same methods as described above. Both compounds were soluble in ethanol producing a clear and colorless solution. The compounds were readily soluble in deionized, distilled water with no particles observed and produced a clear colorless homogeneous solution. The rubusoside to praziquantel mole ratio is 0.078 to 0.016, which is also a 4.86:1 ratio.

| Material | Molecular Weight | Weight | Milli moles | Equivalents |
| --- | --- | --- | --- | --- |
| Rubusoside | 642.74 | 50 mg | 0.078 | 4.86 |
| Praziquantel | 312.41 | 5 mg | 0.016 | 1.00 |

EXAMPLE 31—Tadalafil:Stevioside

Tadalafil is soluble in chloroform and considered insoluble in water. In this example, the following steps were performed. Step 1: In an oven-dried single-neck RB flask equipped with a magnetic stir bar and septa tadalafil and stevioside were added in a 1:3 molar ratio as indicated below. About 2.0 mL of 85% ethanol was added at ambient temperature. It is noted that no difference had been observed in results with the use of 95% ethanol, therefor for the examples 85% ethanol was used.

| Material | Molecular Weight | Weight | Milli moles | Equivalents |
| --- | --- | --- | --- | --- |
| Tadalafil T-80 | 389.4 | 5 MG | 0.01248 | 1.00 |
| Stevioside | 804.87 | 31 MG | 0.03852 | 3.00 |

Ethanol:Denatured: 2 mL
Water:DI: 2 mL

When ethanol was added, the solution became hazy with solids present; the solution had a pH of about 5.5. The reaction mixture was vigorously stirred at room temperature for 30 min. Most reactions are very light hazy or visible solid particles present. 150 µL of 0.1N citric acid was added and the solution became clear and homogeneous having a pH of about 5.2. Ethanol was removed using a rotary evaporator under reduced pressure at 35° C. bath temperature. The white solid was dried over a high vacuum for 1 to 2 hours to remove ethanol completely by determining no further weight loss.

Step 2: To the above mixture, a magnetic stir bar was added and dissolved in Water (~2.0 mL) at room temperature producing a white turbid solution having a pH of about 3.0. To this solution, 50 µL of 0.1 N citric acid was added. NMR was performed as described in the examples above indicating that a complex had not formed.

The same experiment was repeated at a 1:3 molar ratio, only this time no citric acid was added during step 1 (the solution had a pH of about 5.5). The 85% ethanol-tadalafil-stevioside solution again turned hazy with solids present. The solution was dried to remove ethanol until no further drying was observed as described previously.

The dried powder was then dissolved in 2.0 mL water and formed a white turbid solution having a pH of 6.1 to which 200 µL of 0.1 N HCl was added in 100 µL increments, lowering the pH to 2.5 after the addition of 200 µL. The solution remained hazy. A complex was formed, but it was not 100% soluble. The experiments show that with the acid addition, there is an improvement in solubility in water (about a 2.3% improvement in water solubility).

The same experiment was performed using a 1:10 molar ratio, and also using a buffer.

| Material | Molecular Weight | Weight | Milli moles | Equivalents |
|---|---|---|---|---|
| Tadalafil | 389.4 | 5 MG | 0.01248 | 1.00 |
| Stevioside | 804.87 | 103.3 MG | 0.03852 | 10.00 |

Ethanol:Denatured: 2 mL
Water:DI: 2 mL

Before adding the buffer, the ethanol solution was hazy with particles present; the solution had a pH of about 5.5. 200 µL of a 9.4 pH 0.1 M sodium carbonate and carbonate solution, raising the pH of the overall solution to about 6.4. The solution remained hazy with solid particles visible. The solution was dried as before and then 2.0 mL water was added to solubilize the solid. The water solution appeared white and turbid and had a pH of about 9.5. NMR performed as described above showed no evidence of complex formation between stevioside and tadalafil at this molar ratio with the addition of a buffer.

Another experiment using 1:10 molar equivalents of tadalafil to stevioside was performed as follows.

| Material | Molecular Weight | Weight | Milli moles | Equivalents |
|---|---|---|---|---|
| Tadalafil | 389.4 | 5 MG | 0.01248 | 1.00 |
| Stevioside | 804.87 | 103.3 MG | 0.03852 | 10.00 |

Ethanol:Denatured: 2 mL
Water:DI: 2 mL

The stevioside and tadalafil 1:10 molar ratio had 85% ethanol added and the solution stirred for about 30 minutes. The solids slowly became soluble and produced a clear homogeneous solution having a pH of about 5.0. No solids appeared present. The solution was dried as previously described.

The dried powder was dissolved in 2 mL water and formed a white turbid solution having a pH of about 6.0. 120 µL of the carbonate and bicarbonate buffer (pH 9.4) was added raising the pH to about 7.2. No discernable change in the appearance of the liquid was seen and no evidence of improved solubility by NMR.

NMR analysis of the dried powder when solubilized in D20 indicated that the compounds at a 1:10 ratio formed no complex.

In another experiment, a 1:5 ratio of Tadalafil to Tween 80 was tried as follows.

| Material | Molecular Weight | Weight | Milli moles | Equivalents |
|---|---|---|---|---|
| Tadalafil | 389.4 | 10 MG | 0.02568 | 1.00 |
| Tween-80 | 1310 | 168.2 MG | 0.1284 | 5.00 |

Ethanol:Denatured: 2 mL
Water:DI: 2 mL

A 5:1 molar ratio of Tween 80 and tadalafil were dissolved with 85% ethanol and stirred for about 30 minutes, at which point it appeared as a light and turbid solution. The solution was dried as previously described. A clear sticky liquid gel was formed after drying.

In step 2, the gel was dissolved in water and stirred at room temperature for 30 minutes. It was noted that after the first 2-3 minutes, the solution became clear and homogeneous with no precipitate. However, after 3 minutes the solution slowly turned hazy, eventually becoming a white and turbid solution at a pH of about 4.6. The pH was adjusted to about 3.0 using 50 µL 0.1 N HCl. No visible change occurred in the solution. When the white turbid solution was analyzed by NMR (10-12 mg drug complex in 0.5 mL D20 was used in all the examples), trace peaks were observed indicating some complex had formed, but the amount was indeterminable. Nevertheless, the peaks indicate a shift in solubility when using an acid.

Another experiment was performed using a 1:10 ratio of tadalafil and a surfactant as follows.

As before, 85% ethanol was added to the flask having the tadalafil and Poloxamer 188 (P-188) surfactant in a 1:10 ratio as follows.

| Material | Molecular Weight | Weight | Milli moles | Equivalents |
|---|---|---|---|---|
| Tadalafil | 389.4 | 10 MG | 0.02568 | 1.00 |
| P-188 | 8,400 | 215.7 MG | 0.02568 | 10.00 |

Ethanol:Denatured: 2 mL
Water:DI: 2 mL

The 85% ethanol was stirred with the tadalafil and P-188 for 30 minutes. The reaction mixture became a white turbid solution with visible solid particles. The solution was heated to about 45° C. and yielded a clear homogeneous solution within 2 to 3 minutes. The reaction mixture was allowed to cool to room temperature and stirred for 10 minutes; it remained clear and homogenous. The solution was then dried as described before.

The dried mixture was dissolved in water and formed a turbid solution having a pH of about 6.1. When the mixture was heated to 60° C., no change in the white turbid solution was observed. The solution was cooled to room temperature with stirring and 200 µL of 0.1 N HCl was added to adjust the pH to about 2.0. However, no change to the white turbid solution occurred. The mixture then was heated to 60° C., but again no change in the solution's appearance was seen. NMR analysis indicated that no complex was formed.

Another experiment was performed using a 1:10:5 molar ratio of tadalafil:P188:stevioside in 85% (denatured) ethanol as follows.

| Material | Molecular Weight | Weight | Milli moles | Equivalents |
|---|---|---|---|---|
| Tadalafil | 389.4 | 10 MG | 0.02568 | 1.00 |
| P-188 | 8,400 | 161.7 MG | 0.02568 | 10.00 |
| Stevioside | 804.87 | 103.3 | 0.1284 | 5.00 |

Ethanol:Denatured: 3 mL
Water:DI: 3 mL

Tadalafil and stevioside were dissolved in 85% ethanol and stirred for about 30 minutes; a white turbid solution was observed. The turbid solution was heated to 60° C. The reaction mixture cooled to room temperature and P-188 was added at once and stirred for 0.5 h, with no change in solution. The solution was then heated to 60° C., but no change in solution was observed. Added 99.5% methanol (2.0 mL) and heated to 60° C., but no visible change to the white turbid solution was observed. The 3 mL mixture had 2.0 mL 99.5% methanol added; the solution was then heated to 60° C., with no change in the white turbid solution. The solution was then dried as previously described.

To the dried mixture, 3 mL of water was added and stirred for about 30 minutes; the mixture formed a white turbid solution. The solution was heated to 60° C. but did not change the appearance of the solution. The heated solution was cooled to room temperature, and then 200 µL 0.1 N citric acid was added to adjust the pH to about 3.0. The addition of citric acid did not alter the appearance of the solution. The citric acid-containing solution was heated to 90° C. with stirring, but still produced to change in the appearance of the solution. When analyzed by NMR, low-intensity drug peaks evidence complex formation. A change of polarity from acid addition improves complex formation and therefore solubility.

Another experiment was performed using a 1:5 molar ratio of tadalafil to Tween 20 as follows.

| Material | Molecular Weight | Weight | Milli moles | Equivalents |
|---|---|---|---|---|
| Tadalafil | 389.4 | 10 MG | 0.02568 | 1.00 |
| T20 | 1228 | 161.7 MG | 0.1284 | 5.00 |

Ethanol:Denatured: 2 mL
Water:DI: 2 mL

The tadalafil and Tween 20 (T20) were dissolved in 85% ethanol and stirred for about 30 minutes. The compounds were observed to slowly form a clear homogenous solution. The solution mixture was dried using the methods previously described.

The dried mixture was then dissolved in 2.0 mL of water for 30 minutes, wherein it formed a white turbid solution with solids still visible in the solution. The mixture was then heated to 60° C., without a change in appearance. NMR was performed on about 0.5 mL of the mixture but at best only low peaks were observed, again indicating poor complex formation when using the surfactant.

The remaining portion was cooled to room temperature and 10 mg citric acid monohydrate was added making the pH about 2.5. The solution remained white and turbid. The solution was then heated to 60° C., but no change in appearance was observed. NMR revealed only low-intensity drug peaks suggesting the formation of some of the drug in a complex.

Another experiment was performed using 1:20:5 of tadalafil:glycerol:stevioside as follows.

| Material | Molecular Weight | Weight | Milli moles | Equivalents |
|---|---|---|---|---|
| Tadalafil | 389.4 | 10 MG | 0.02568 | 1.00 |
| Glycerol | 92.09 | 23.64 MG | 0.5136 | 20.00 |
| Stevioside | 804.87 | 103.3 | 0.1284 | 5.00 |

Ethanol:Denatured: 3 mL
Water:DI: 3 mL

The tadalafil, glycerol, and stevioside were added to a flask to which 3.0 mL of 85% ethanol was added. The mixture was stirred at room temperature for 30 minutes forming a hazy solution with visible particles present. 100 µL ACS grade methanol was added and stirred for 20 minutes and the solution became clear and homogeneous. The clear mixture was dried as previously described and produced a white powder.

The dried mixture was solubilized in 3.0 mL water and stirred for about 30 minutes at room temperature. A white turbid solution formed having a pH of 5.8. 1.5 mL of the mixture had 0.1 NaOH solution added adjusting the final pH to about 7.4. This solution remained a white turbid solution. When examined by NMR no drug peaks were observed that would indicate complex formation between tadalafil and the other components.

The other 1.5 mL portion had 10 mg of citric acid monohydrate added and stirred for about 30 minutes at room temperature. The final solution had a pH of about 3.0. When assessed by NMR, only low-intensity drug peaks (~2-3%) were observed. The acid appears to improve complex formation and solubility.

Another experiment was performed using a 1:30:5 molar ratio of tadalafil:glycerol:stevioside as follows.

| Material | Molecular Weight | Weight | Milli moles | Equivalents |
|---|---|---|---|---|
| Tadalafil | 389.4 | 10 MG | 0.02568 | 1.00 |
| Glycerol | 92.09 | 70.9 MG | 0.7704 | 30.00 |
| Stevioside | 804.87 | 103.3 | 0.1284 | 5.00 |

Methanol:ACS grade: 3 mL
Water:DI: 3 mL

Tadalafil and stevioside were dissolved in 3.0 mL methanol (ACS grade is ≥99.5% methanol, Sigma Aldrich) and stirred at room temperature for about 30 minutes producing a white turbid solution. 50 µL 85% ethanol was added and the mixture was stirred for another 20 minutes at about 30° C. The mixture became less white and turbid. At this point, the mixture was dried as previously described.

The dried mixture was then dissolved in 3.0 mL water and stirred for about 30 minutes. The mixture had a pH of about 5.8. To this solution, 20 mg of citric acid monohydrate was added reducing the pH to about 3.0. A white turbid reaction was seen. NMR analysis revealed some low peaks indicating complex formation. The experiment indicates that by reducing the solution's pH, there is an improvement in drug solubility and thus, complex formation.

EXAMPLE 32—Vardenafil HCl and Stevioside

In this experiment, a complex was tried using vardenafil HCl, stevioside, denatured ethanol, and water as follows. It was known that vardenafil HCl is poorly water-soluble (0.11 mg/mL water). While it is soluble in DMSO at 28° C., solids remain present at 22° C. and it is insoluble in chloroform.

| Material | Molecular Weight | Weight | Milli moles | Equivalents |
|---|---|---|---|---|
| Vardenafil HCl | 525.1 | 5 MG | 0.00952 | 1.00 |
| Stevioside | 804.87 | 76.6 MG | 0.09522 | 10.00 |

Ethanol:Denatured
Water:DI

Both vardenafil HCl and the stevioside dissolved in 2.0 mL denatured ethanol at a 1:10 molar ratio easily at room temperature producing a clear solution. The reaction mixture was stirred for about 30 minutes.

The ethanol was removed by drying as described previously at 35° C. until no change of weight was observed. The powder was then dissolved in 2.0 mL water and produced a clear solution. When assessed by NMR, peaks were observed corresponding to complex formation between the sugar and vardenafil HCl and 100% solubility of the complex.

EXAMPLE 33—Alprostadil-Stevioside

In this experiment, a complex was tried using alprostadil, stevioside, denatured ethanol, and water as follows. Alprostadil is soluble in DMSO. Alprostadil has the chemical name: (1R,2R,3R)-3-Hydroxy-2-[(E)-(3S)-3-hydroxy-1-octenyl]-5-oxocyclopentane heptanoic acid and is also referred to as prostaglandin E1. Alprostadil is considered insoluble in water.

| Material | Molecular Weight | Weight | Milli moles | Equivalents |
|---|---|---|---|---|
| VITAROS | 354.48 | 5 MG | 0.01411 | 1.00 |
| Stevioside | 804.87 | 113 MG | 0.14105 | 10.00 |

Ethanol:Denatured
Water:DI

Both alprostadil and stevioside dissolved in 2.0 mL denatured ethanol at a 1:10 molar ratio easily at room temperature producing a clear homogeneous solution (pH of about 4.9). The reaction mixture was stirred for about 30 minutes.

The ethanol was removed by drying as described previously at 35° C. until no change of weight was observed. The powder was then dissolved in 2.0 mL water and produced a clear homogeneous solution (pH of about 5.8). When assessed by NMR, peaks were observed corresponding to complex formation between the sugar and alprostadil and 100% solubility of the complex.

In some cases, a moderately soluble compound can be made more soluble by complexation with a sugar as defined herein at the same ratios of sugar and compound as set forth herein. Such is particularly important for topical application for the solubility of a compound as it is transported across the skin barrier for purposes of in vivo uptake. For example, sildenafil has moderate solubility, but it can be enhanced by the methods used herein. Without being limited to any theory, it is believed that as the molar ratio of the sugar to a moderately soluble drug increases the solubility of the resulting complex approaches that of the sugar alone, because of the presence of the sugars in the complex, the complex will have greater solubility than the drug alone.

EXAMPLE 34—Avanafil-Stevioside

In this experiment, a 1:10 molar ratio of avanafil to stevioside in denatured ethanol was tested as follows. Avanafil is soluble in DMSO. Avanafil, sildenafil, tadalafil, vardenafil, and udenafil are all PDE5 inhibitors.

| Material | Molecular Weight | Weight | Milli moles | Equivalents |
|---|---|---|---|---|
| Avanafil | 483.95 | 5 MG | 0.01033 | 1.00 |
| Stevioside | 804.87 | 83.15 MG | 0.10332 | 10.00 |

Ethanol:Denatured
Water:DI

The compounds slowly solubilized in about 15 to 20 minutes with stirring for 30 minutes. The compounds eventually formed a clear and homogeneous solution having a pH of about 5.2. The solution was dried to remove the ethanol until no further change of weight was observed.

The dried powder was dissolved in 2.0 mL water as previously described with stirring and formed a clear homogeneous solution having a pH of about 6.2. NMR showed that a complex had formed and 100% solubility of the compound.

EXAMPLE 35—Udenafil-Stevioside

In this experiment, a 1:10 molar ratio of udenafil to stevioside was solubilized in denatured ethanol as follows. Udenafil is known to be soluble in DMSO. It has a water solubility of about 0.0798 mg/mL.

| Material | Molecular Weight | Weight | Milli moles | Equivalents |
|---|---|---|---|---|
| Udenafil | 516.66 | 5 MG | 0.00968 | 1.00 |
| Stevioside | 804.87 | 77.9 MG | 0.0968 | 10.00 |

Ethanol:Denatured
Water:DI

The two compounds were observed to form a clear colorless homogeneous solution after 30 minutes of stirring when dissolved in 2.0 mL 85% ethanol. The solution had a pH of about 5.5. The solution was dried to a power as previously described.

The powder was dissolved in 2.0 mL water and formed a clear solution with stirring. However, white particles started forming after 1 hour. NMR showed that a complex had formed that made the udenafil and stevioside complex soluble.

Accordingly, in one embodiment, there is provided a method for increasing the aqueous solubility of a moderately soluble compound, which method comprises forming a stable complex of said compound with a sugar as defined herein.

Embodiments

The following are embodiments presenting various methods and complexes formed by the methods.

Embodiment 1. A water-soluble aggregate comprising a sugar and a poorly water-soluble drug, which aggregate comprises:

a molar ratio of up to about 5 moles of the sugar for each mole of said poorly water-soluble drug, wherein the sugar is one or more of rubusoside, dulcoside B, dodecyl-β-D-maltoside, stevioside, or rebaudioside A, provided that said water-soluble aggregate has at least a five (5) fold increase in the water solubility of said poorly soluble drug at 20° C. as compared to the water solubility of said drug not in said water-soluble aggregate; and further provided that a maximum amount of the sugar in a daily unit dose of said aggregate is no more than about 10 mg/kg.

Embodiment 2. The water-soluble aggregate of Embodiment [1], wherein the sugar is rubusoside.

Embodiment 3. The water-soluble aggregate of Embodiments [1] or [2], wherein the poorly water-soluble drug is one or more of sildenafil, tadalafil, vardenafil, avanafil, or a pharmaceutically acceptable salt of any thereof.

Embodiment 4. The water-soluble aggregate of any of Embodiments [1] or [3], wherein the sugar is rubusoside, rebaudioside A, dodecyl-β-D-maltoside, dulcoside B, or stevioside.

Embodiment 5. The water-soluble aggregate of any of Embodiments [1], [3], or [4], wherein the amount of the sugar in the daily unit dose is no more than 5 mg/kg.

Embodiment 6. The water-soluble aggregate of any of Embodiments [1], [3], or [4], wherein the amount of the sugar in the daily unit dose is no more than about 280 mg.

Embodiment 7. The water-soluble aggregate of any of Embodiments [1], [3] or [4], wherein said water-soluble aggregate comprises a molar ratio of from about 2 to about 5 moles of the sugar for each mole of said poorly water-soluble drug.

Embodiment 8. The water-soluble aggregate of any of Embodiments [1], [3] or [4], wherein said water-soluble aggregate comprises a molar ratio of from about 2 to about 4.5 moles of the sugar for each mole of said poorly water-soluble drug.

Embodiment 9. The water-soluble aggregate of Embodiment 8, wherein said water-soluble aggregate comprises a molar ratio of about 3 moles of the sugar for each mole of said poorly water-soluble drug.

Embodiment 10. The water-soluble aggregate of any of the above Embodiments, wherein said water-soluble aggregate is stable in water at pH 8.5 for at least 2 hours.

Embodiment 11. The water-soluble aggregate of any of the above Embodiments, wherein said water-soluble aggregate is stable in water at pH 4 for at least 2 hours.

Embodiment 12. A dried form of the water-soluble aggregate of any of the above Embodiments, wherein the dried form is stable at 30° C. for at least 90 days.

Embodiment 13. The water-soluble aggregate of any of the above Embodiments, wherein the water-soluble aggregate is in the form of a powder, a tablet, an orally disintegrating tablet, a capsule, a liquid, a gel, a thin film, a lozenge, an effervescent powder or tablet, an emulsion, or formulated for parenteral administration.

Embodiment 14. The water-soluble aggregate of any of the above Embodiments, wherein the formulation for parenteral administration is to be administered intradermally, subcutaneously, intramuscularly, intraperitoneally, or intravenously.

Embodiment 15. The water-soluble aggregate of any of the above Embodiments, wherein the water-soluble aggregate is in the form of a thin film, an effervescent powder or tablet, a syrup, a solution, an elixir, an emulsion, a chewing gum, a lollipop, a sublingual drop, a soft gel, or a tincture.

Embodiment 16. A water-soluble aggregate comprising a sugar and a poorly water-soluble drug, which water-soluble aggregate comprises:
a molar ratio of about 3 moles of the sugar for each mole of said poorly water-soluble drug, wherein the sugar is one or more of rubusoside, rebaudioside A, dulcoside B, dodecyl-β-D-maltoside (DDM), or stevioside;
wherein said water-soluble aggregate is stable in water at pH 8.5 and at pH 4.0 for at least 2 hours each;
provided that said water-soluble aggregate has at least a five (5) fold increase in the water solubility of said poorly soluble drug at 20° C. as compared to the water solubility of said poorly water-soluble drug not in the water-soluble aggregate; and
further provided that a maximum amount of the sugar in a daily unit dose of said water-soluble aggregate is no more than about 280 mg.

Embodiment 17. A method of making a water-soluble aggregate comprising a sugar and a poorly water-soluble drug, the method comprising the steps of
admixing, in at least 85% ethanol, the sugar with the poorly water-soluble drug in a molar ratio of from about 2 to about 5 moles of the sugar for each mole of said poorly water-soluble drug until solubilized thereby forming the water-soluble aggregate, wherein formation of the water-soluble aggregate can be determined by nuclear magnetic resonance spectroscopy, and wherein the sugar is one or more of rubusoside, rebaudioside A, dulcoside B, dodecyl-β-D-maltoside (DDM), or stevioside; and wherein the admixing step is optionally performed with a pharmaceutically acceptable acid; and
optionally drying the water-soluble aggregate.

Embodiment 18. The method of Embodiment 17, wherein the sugar is rubusoside or stevioside.

Embodiment 19. The method of any of Embodiments or [18], wherein the poorly water-soluble drug is one or more of sildenafil, tadalafil, vardenafil, avanafil, or a pharmaceutically acceptable salt of any thereof.

Embodiment 20. The method of any of Embodiments to [19], further comprising drying the water-soluble aggregate.

Embodiment 21. The method of Embodiment [20], wherein the dried water-soluble aggregate is resolubilized in a liquid.

Embodiment 22. The method of Embodiment [17], wherein the admixing step is in the presence of a sufficient amount of a pharmaceutically acceptable acid to solubilize and render the reaction mixture homogeneous and clear.

Embodiment 23. The method of Embodiment [22], wherein the pharmaceutically acceptable acid is acetic acid, ascorbic acid, aspartic acid, citric acid, formic acid, fumaric acid, gluconic acid, glutamic acid, glutaric acid, glycolic acid, hydrochloric acid, lactic acid, lauric acid, maleic acid, malic acid, malonic acid, nitric acid, oleic acid, oxalic acid, palmitic acid, propionic acid, salicylic acid, stearic acid, succinic acid, or tartaric acid.

Embodiment 24. The method of Embodiment [17], wherein said formed water-soluble aggregate comprises a molar ratio of from about 2 to about 5 moles of the sugar for each mole of said poorly water-soluble drug.

Embodiment 25. The method of any of Embodiments [17] to [24], wherein the sugar is rubusoside or stevioside.

Embodiment 26. The method of any of Embodiments to [25], wherein said formed water-soluble aggregate comprises a molar ratio of from about 2 to about 4.5 moles of the sugar for each mole of said poorly water-soluble drug.

Embodiment 27. The method of Embodiment [26], wherein the sugar is rubusoside or stevioside.

Embodiment 28. The method of Embodiment [24], wherein said formed water-soluble aggregate comprises a molar ratio of about 3 moles of the sugar for each mole of said poorly water-soluble drug.

Embodiment 29. The method of Embodiment [28], wherein the sugar is rubusoside or stevioside.

Embodiment 30. The method of Embodiment [17,] wherein said formed water-soluble aggregate is stable in water at pH 8.5 for at least 2 hours.

Embodiment 31. The method of Embodiment [17], wherein said formed water-soluble aggregate is stable in water at pH 4 for at least 2 hours.

Embodiment 32. The method of Embodiment [20], further comprising drying the water-soluble aggregate by freeze-drying or lyophilizing.

Embodiment 33. The method of Embodiment [32], wherein the dried water-soluble aggregate is formulated into a pill or a pharmaceutically acceptable liquid.

Embodiment 34. A water-soluble complex comprising a poorly water-soluble drug and a sugar (DTG), wherein the drug has hydrogen bonding of the poorly water-soluble drug to the sugar forming a water-soluble complex of formula (I):

$$[DTG]_p Drug, \qquad (I)$$

wherein p is the molar ratio of up to about 20 moles of the sugar (DTG) for each mole of said drug, wherein the sugar is one or more of rubusoside, dulcoside A, dulcoside B, sucrose, D-fructose, sucralose, rebaudioside A, rebaudioside B, rebaudioside D, stevioside, stevia, n-octyl glucose, n-dodecyl-β-D-maltoside, Advantame®, neotame, thaumatin, saccharin, sucralose, a steviol glycoside, Lou Han Guo, aspartame, acesulfame potassium, or allulose, wherein the drug is an erectile dysfunction drug, and provided that said water-soluble complex has at least a five (5) fold increase in the water solubility of said Compound at 20° C. as compared to the water solubility of said Compound not in said water-soluble complex.

Embodiment 35. The water-soluble complex of Embodiment comprising a molar ratio of up to about 5 moles of the sugar for each mole of said poorly water-soluble drug, wherein the sugar is one or more of rubusoside, dulcoside B, dodecyl-β-D-maltoside, stevioside, or rebaudioside A, provided that said the water-soluble complex has at least a five (5) fold increase in the water solubility of said poorly soluble drug at 20° C. as compared to the water solubility of said drug not in said water-soluble complex; and further provided that a maximum amount of the sugar in a daily unit dose of said complex is no more than about 10 mg/kg.

Embodiment 36. The water-soluble complex of any of Embodiments or [35], wherein the poorly water-soluble drug is one or more of alprostadil, sildenafil, tadalafil, vardenafil, avanafil, a pharmaceutically acceptable salt or polymorph of any thereof.

Embodiment 37. The water-soluble complex of any of Embodiments to [36], wherein the sugar is rubusoside, rebaudioside A, dodecyl-β-D-maltoside, dulcoside B, or stevioside.

Embodiment 38. The water-soluble complex of any of Embodiments to [37], wherein the amount of the sugar in the daily unit dose is no more than 5 mg/kg.

Embodiment 39. The water-soluble complex of claim 5, wherein the amount of the sugar in the daily unit dose is no more than about 280 mg.

Embodiment 40. The water-soluble complex of any of Embodiments to [39], wherein said water-soluble complex comprises a molar ratio of about 2 to about 5 moles of the sugar for each mole of the drug.

Embodiment 41. The water-soluble complex of any of Embodiments to [39], wherein said water-soluble complex comprises a molar ratio of from about 2 to about 4.5 moles of the sugar for each mole of said poorly water-soluble drug.

Embodiment 42. The water-soluble complex of Embodiment [41], wherein said water-soluble complex comprises a molar ratio of about 3 moles of the sugar for each mole of the drug.

Embodiment 43. The water-soluble complex of any of Embodiments to [42], wherein said water-soluble complex is stable in water at pH 8.5 for at least 2 hours.

Embodiment 44. The water-soluble complex of any of Embodiments to [42], wherein said water-soluble complex is stable in water at pH 4 for at least 2 hours.

Embodiment 45. A dried form of the water-soluble complex of any of Embodiments to [44], wherein the dried form is stable at 30°C. for at least 90 days.

Embodiment 46. The water-soluble complex of any of Embodiments to [44], wherein the water-soluble complex is in a form for oral administration such as a powder, a tablet, an orally disintegrating tablet, a capsule, a liquid, a gel, a thin film, a lozenge, an effervescent powder or tablet, or an emulsion, or formulated for parenteral administration.

Embodiment 47. The water-soluble complex of Embodiment [346], wherein the formulation for parenteral administration is to be administered intradermally, subcutaneously, intranasally, intramuscularly, or intraperitoneally.

Embodiment 48. The water-soluble complex of any of Embodiments to [45], wherein the water-soluble complex is in the form of a thin film, an effervescent powder or tablet, a syrup, a solution, an elixir, an emulsion, a chewing gum, a lollipop, a sublingual drop, a soft gel, or a tincture.

Embodiment 49. A water-soluble complex comprising a sugar and a poorly water-soluble drug, which water-soluble complex comprises:

a molar ratio of about 3 moles of the sugar for each mole of said poorly water-soluble drug, wherein the sugar is one or more of rubusoside, rebaudioside A, dulcoside B, dodecyl-β-D-maltoside (DDM), or stevioside;

wherein said water-soluble complex is stable in water at about pH 8.5 and about pH 4.0 for at least 2 hours each;

provided that said water-soluble complex has at least a five (5) fold increase in the water solubility of said poorly soluble drug at 20° C. as compared to the water solubility of said poorly water-soluble drug not in the water-soluble complex; and further provided that a maximum amount of the sugar in a daily unit dose of said water-soluble complex is no more than about 280 mg.

Embodiment 50. A method of making a water-soluble complex comprising a sugar and a poorly water-soluble drug, the method comprising the steps of admixing, in at least 85% ethanol, the sugar with the poorly water-soluble drug in a molar ratio of from about 1 to about 20 moles of the sugar for each mole of said poorly water-soluble drug until solubilized thereby forming the water-soluble complex, wherein formation of the water-soluble complex can be determined by nuclear magnetic resonance (NMR) spectroscopy, and wherein the sugar is one or more of rubusoside, rebaudioside A, dulcoside B, dodecyl-β-D-maltoside (DDM), or stevioside; and wherein the admixing step is optionally performed with a pharmaceutically acceptable acid, base, buffer or surfactant; and optionally drying the water-soluble complex.

Embodiment 51. The method of Embodiment [50], wherein the sugar is rubusoside or stevioside.

Embodiment 52. The water-soluble complex of any of Embodiments to [51], wherein the poorly water-soluble drug is one or more of alprostadil, sildenafil, tadalafil, vardenafil, avanafil, or a pharmaceutically acceptable salt of any thereof.

Embodiment 53. The method of Embodiment [50], further comprises drying the water-soluble complex.

Embodiment 54. The method of Embodiment [53], wherein the dried water-soluble complex is resolubilized in water optionally with a pharmaceutically acceptable acid, base, buffer, or surfactant.

Embodiment 55. The method of Embodiment [50], wherein the admixing step is in the presence of a sufficient amount of a pharmaceutically acceptable acid to solubilize and render the reaction mixture homogeneous and clear.

Embodiment 56. The method of Embodiment [55], wherein the pharmaceutically acceptable acid is acetic acid, ascorbic acid, aspartic acid, citric acid, formic acid, fumaric acid, gluconic acid, glutamic acid, glutaric acid, glycolic acid, hydrochloric acid, lactic acid, lauric acid, maleic acid, malic acid, malonic acid, nitric acid, oleic acid, oxalic acid, palmitic acid, propionic acid, salicylic acid, stearic acid, succinic acid, or tartaric acid.

Embodiment 57. The method of Embodiment [50], wherein said formed water-soluble complex comprises a molar ratio of about 2 to about 20 moles of the sugar for each mole of said poorly water-soluble drug.

Embodiment 58. The method of Embodiment [57], wherein the sugar is rubusoside or stevioside.

Embodiment 59. The method of Embodiment [50], wherein said formed water-soluble complex comprises a molar ratio of about 2 to about 10 moles (e.g., 4.5 moles) of the sugar for each mole of said poorly water-soluble drug.

Embodiment 60. The method of Embodiment [59], wherein the sugar is rubusoside or stevioside.

Embodiment 61. The method of Embodiment [57], wherein said formed water-soluble complex comprises a molar ratio of about 2 to about 5 moles of the sugar for each mole of said poorly water-soluble drug.

Embodiment 62. The method of Embodiment [61], wherein the sugar is rubusoside or stevioside.

Embodiment 63. The method of Embodiment [50], wherein said formed water-soluble complex is stable in water at pH 8.5 for at least 2 hours.

Embodiment 64. The method of Embodiment [50], wherein said formed water-soluble complex is stable in water at pH 4 for at least 2 hours.

Embodiment 65. The method of Embodiment [53], wherein the method further comprises drying the water-soluble complex by freeze-drying or lyophilizing.

Embodiment 66. The method of Embodiment [65], wherein the dried water-soluble complex is formulated into a pill or a pharmaceutically acceptable liquid.

The invention claimed is:

1. A water-soluble complex comprising:
   a poorly water-soluble drug selected from sildenafil, tadalafil, vardenafil, avanafil, or a pharmaceutically acceptable salt of any thereof; and
   a sugar selected from rubusoside, dulcoside B, n-dodecyl-β-D-maltoside, stevioside, rebaudioside A, rebaudioside B, rebaudioside D, stevia, n-octyl glucose, advantame, neotame, thaumatin, saccharin, sucralose, a steviol glycoside, Lou Han Guo, aspartame, acesulfame potassium, or allose,
   provided that said water-soluble complex has at least a five (5) fold increase in the water solubility of said poorly soluble drug at 20° C. as compared to the water solubility of said drug not in said water-soluble complex, said water-soluble complex having been formed by dissolving the sugar and poorly water-soluble drug in a solvent of ethanol or methanol or a combination thereof, drying the complex and dissolving the dried complex in water.

2. A water-soluble complex comprising:
   a poorly water-soluble drug selected from sildenafil, tadalafil, vardenafil, avanafil, or a pharmaceutically acceptable salt of any thereof; and
   a sugar selected from rubusoside, dulcoside B, dodecyl-β-D-maltoside, stevioside, and rebaudioside A having a molar ratio of said sugar to said poorly soluble drug of up to about 5:1,
   provided that said water-soluble complex has at least a five (5) fold increase in the water solubility of said poorly soluble drug at 20° C. as compared to the water solubility of said drug not in said water-soluble complex, said water-soluble complex having been formed by dissolving the sugar and poorly water-soluble drug in a solvent of ethanol or methanol or a combination thereof, drying the complex and dissolving the dried complex in water; and
   further wherein the maximum amount of the sugar in a daily unit dose of said complex is no more than about 10 mg/kg.

3. The water-soluble complex of claim 2, wherein the maximum amount of the sugar in the daily dose of said complex to a subject does not exceed a Generally Regarded As Safe (GRAS) amount.

4. The water-soluble complex of claim 2, wherein the molar ratio of the sugar is from about 1 to about 10 moles for each mole of said poorly water-soluble drug.

5. The water-soluble complex of claim 1, wherein said sugar comprises rubusoside and the poorly water-soluble drug is sildenafil.

6. The water-soluble complex of claim 1, wherein said sugar comprises rubusoside and the poorly water-soluble drug is tadalafil.

7. The water-soluble complex of claim 1, wherein said sugar comprises rubusoside and the poorly water-soluble drug is vardenafil.

8. The water-soluble complex of claim 1, wherein said sugar comprises rubusoside and the poor water-soluble drug is avanafil.

9. The water-soluble complex of claim 1, wherein said sugar comprises dulcoside B and the poorly water-soluble drug is sildenafil.

10. The water-soluble complex of claim 1, wherein said sugar comprises dulcoside B and the poorly water-soluble drug is tadalafil.

11. The water-soluble complex of claim 1, wherein said sugar comprises dulcoside B and the poorly water-soluble drug is vardenafil.

12. The water-soluble complex of claim 1, wherein said sugar comprises dulcoside B and the poorly water-soluble drug is avanafil.

13. The water-soluble complex of claim 1, wherein said sugar comprises stevioside and the poorly water-soluble drug is sildenafil.

14. The water-soluble complex of claim 1, wherein said sugar comprises stevioside and the poorly water-soluble drug is tadalafil.

15. The water-soluble complex of claim 1, wherein said sugar comprises stevioside and the poorly water-soluble drug is vardenafil.

16. The water-soluble complex of claim 1, wherein said sugar comprises stevioside and the poor water-soluble drug is avanafil.

17. The water-soluble complex of claim 1, wherein said sugar comprises rebaudioside A and the poorly water-soluble drug is sildenafil.

18. The water-soluble complex of claim 1, wherein said sugar comprises rebaudioside A and the poorly water-soluble drug is tadalafil.

19. The water-soluble complex of claim 1, wherein said sugar comprises rebaudioside A and the poorly water-soluble drug is vardenafil.

20. The water-soluble complex of claim 1, wherein said sugar comprises rebaudioside A and the poor water-soluble drug is avanafil.

21. A method of improving solubility of a poorly water soluble drug comprising:
admixing the poorly water soluble drug with a sugar in a solvent; and wherein if admixing fails to fully solubilize the poorly water-soluble drug, further adjusting pH with a pharmaceutically acceptable acid or base;
drying the solubilized compound to obtain a powder of a water-soluble complex; and
dissolving the dried powder of the water-soluble complex;
wherein the poorly water-soluble drug is sildenafil, tadalafil, vardenafil, avanafil, or a pharmaceutically acceptable salt of any thereof and the solvent is ethanol, methanol or a mixture thereof;
the sugar is rubusoside, dulcoside B, n-dodecyl-β-D-maltoside, stevioside, rebaudioside A, rebaudioside B, rebaudioside D, stevia, n-octyl glucose, advantame, neotame, thaumatin, saccharin, sucralose, a steviol glycoside, Lou Han Guo, aspartame, acesulfame potassium, or allose; and
the water-soluble complex has at least a five (5) fold increase in the water solubility of said poorly soluble drug at 20° C. as compared to the water solubility of said drug not in said water-soluble complex.

22. The method of claim 21, wherein the solvent is ethanol, methanol, a combination of ethanol and methanol, an aqueous ethanol, an aqueous methanol, or a combination of ethanol, methanol, and water.

23. The method of claim 21, wherein an acid is added to the poorly water-soluble drug, the sugar and the solvent.

24. The method of claim 23, wherein the water soluble complex comprises a molar ratio of about 1 to about 10 moles of the sugar for each mole of the poorly water-soluble drug.

25. The water-soluble complex of claim 1, wherein the complex was created in the presence of an acid.

26. The water-soluble complex of claim 1, wherein said water-soluble complex is stable in water at pH 4 for at least 2 hours or is stable in water at a pH of 8.5 for at least 2 hours.

27. A pharmaceutical composition comprising a pharmaceutically acceptable excipient and an amount of a complex of claim 1 sufficient to treat ED.

28. The pharmaceutical composition of claim 27, wherein said composition is selected from a powder, a tablet, an orally disintegrating tablet, a capsule, a liquid, a chewing gum, a lollipop, a sublingual drop, a soft gel, a syrup, a gel, a thin film, a lozenge, an effervescent powder or tablet, an emulsion, or formulated for parenteral administration.

29. A method of treating erectile dysfunction in a subject in need thereof comprising the step of administering a pharmaceutical composition of claim 27.

* * * * *